US012636476B2

(12) United States Patent

Schouenborg

(10) Patent No.: US 12,636,476 B2

(45) Date of Patent: May 26, 2026

(54) METHOD OF IMPLANTATION OF CELL AGGREGATES AND TISSUE FRAGMENTS

(71) Applicant: NEURONANO AB, Karlshamn (SE)

(72) Inventor: Jens Schouenborg, Lund (SE)

(73) Assignee: NEURONANO AB (SE)

( * ) Notice: Subject to any disclaimer, the term of this patent is extended or adjusted under 35 U.S.C. 154(b) by 52 days.

(21) Appl. No.: 18/215,210

(22) Filed: Jun. 28, 2023

(65) Prior Publication Data

US 2023/0338722 A1      Oct. 26, 2023

Related U.S. Application Data

(63) Continuation of application No. 16/073,373, filed as application No. PCT/SE2017/000014 on Feb. 23, 2017, now Pat. No. 11,724,080.

(30) Foreign Application Priority Data

Feb. 26, 2016    (SE) .................................... 1600070-5

(51) Int. Cl.
    *A61M 37/00*      (2006.01)
    *A61B 5/055*      (2006.01)
              (Continued)

(52) U.S. Cl.
    CPC ....... *A61M 37/0069* (2013.01); *A61L 27/222* (2013.01); *A61L 27/3675* (2013.01);
              (Continued)

(58) Field of Classification Search
    CPC ............ A61M 37/0069; A61M 5/3129; A61M 2202/07; A61M 2202/09; A61M 2205/3306; A61M 2210/0693; A61M 2230/08; A61M 2205/04; A61L 27/222; A61L 27/3675; A61L 27/54;

(Continued)

(56) References Cited

U.S. PATENT DOCUMENTS

| | | | |
|---|---|---|---|
| 6,205,359 B1 | 3/2001 | Boveja | ............................. 607/45 |
| 6,772,694 B1 * | 8/2004 | Pearce, III | .............. F42B 12/50 |
| | | | 102/370 |

(Continued)

FOREIGN PATENT DOCUMENTS

| | | |
|---|---|---|
| DE | 39 14 115 A1 | 10/1990 |
| EP | 2 388 022 A1 | 11/2011 |

(Continued)

OTHER PUBLICATIONS

International Search Report mailed May 23, 2017 in corresponding PCT International Application No. PCT/SE2017/000014.

(Continued)

*Primary Examiner* — Chelsea E Stinson
*Assistant Examiner* — Hamza A Darb
(74) *Attorney, Agent, or Firm* — OSTROLENK FABER LLP

(57) ABSTRACT

In a method for implantation of a physically stabilized aggregate of living cells or tissue fragment is injected into a channel provided in soft tissue filled with an aqueous gel. Also discloses are methods of stabilizing such aggregates and fragments and of forming such channel in soft tissue as well as means for carrying out the methods.

12 Claims, 11 Drawing Sheets

(51) Int. Cl.

| | |
|---|---|
| *A61L 27/22* | (2006.01) |
| *A61L 27/36* | (2006.01) |
| *A61L 27/54* | (2006.01) |
| *A61L 31/02* | (2006.01) |
| *A61L 31/04* | (2006.01) |
| *A61M 5/31* | (2006.01) |
| *A61N 1/05* | (2006.01) |
| *A61B 5/00* | (2006.01) |

(52) U.S. Cl.
CPC ............ *A61L 27/54* (2013.01); *A61L 31/022* (2013.01); *A61L 31/04* (2013.01); *A61M 5/3129* (2013.01); *A61N 1/0551* (2013.01); *A61B 5/4893* (2013.01); *A61B 2576/026* (2013.01); *A61M 2202/07* (2013.01); *A61M 2202/09* (2013.01); *A61M 2205/3306* (2013.01); *A61M 2210/0693* (2013.01); *A61M 2230/08* (2013.01)

(58) Field of Classification Search
CPC ..... A61L 31/022; A61L 31/04; A61N 1/0551; A61B 5/055; A61B 5/4893; A61B 2576/026; G16H 30/40
See application file for complete search history.

(56)                    References Cited

U.S. PATENT DOCUMENTS

| | | | | |
|---|---|---|---|---|
| 7,137,969 | B1 | 11/2006 | Mendez | |
| 2002/0064875 | A1 | 5/2002 | Chen et al. | ................... 435/399 |
| 2003/0236573 | A1* | 12/2003 | Evans | ................... A61F 2/4601 623/23.63 |
| 2004/0101518 | A1 | 5/2004 | Vacanti et al. | ............... 424/93.7 |
| 2004/0266000 | A1 | 12/2004 | Offermann et al. | .......... 435/398 |

| | | | | |
|---|---|---|---|---|
| 2005/0226856 | A1 | 10/2005 | Ahlfors | ........................ 424/93.7 |
| 2006/0141000 | A1 | 6/2006 | Mikos et al. | ................. 424/422 |
| 2007/0048292 | A1 | 3/2007 | Morita et al. | ................ 424/93.7 |
| 2009/0060969 | A1 | 3/2009 | Mikos et al. | ................. 424/422 |
| 2009/0112273 | A1 | 4/2009 | Wingeier et al. | ................. 607/3 |
| 2009/0112278 | A1 | 4/2009 | Wingeier et al. | ............... 607/45 |
| 2009/0137946 | A1 | 5/2009 | Nassiri et al. | .................. 604/60 |
| 2010/0041146 | A1 | 2/2010 | Kambayashi et al. | ........ 435/383 |
| 2010/0114069 | A1 | 5/2010 | Trieu | ............................. 604/522 |
| 2010/0297208 | A1 | 11/2010 | Fry et al. | ...................... 424/422 |
| 2011/0087315 | A1 | 4/2011 | Richardson-Burns et al. | ............ 607/116 |
| 2012/0045487 | A1 | 2/2012 | Lahann et al. | ................. 424/400 |
| 2012/0123318 | A1* | 5/2012 | Ek | ........................ A61N 1/0476 604/20 |
| 2012/0132675 | A1 | 5/2012 | Vogt et al. | .................... 222/327 |
| 2013/0296828 | A1* | 11/2013 | Schon | ........................ A61F 2/28 623/23.61 |
| 2014/0024117 | A1 | 1/2014 | Kim et al. | .................... 435/395 |
| 2014/0112894 | A1 | 4/2014 | Zheng et al. | ................ 424/93.7 |
| 2017/0251976 | A1 | 9/2017 | Schouenborg | |

FOREIGN PATENT DOCUMENTS

| | | |
|---|---|---|
| KR | 10-2008-0009911 | 1/2008 |
| WO | WO 2007/028003 A2 | 3/2007 |
| WO | WO 2013/191612 A1 | 12/2013 |
| WO | WO 2016/032384 A1 | 3/2016 |

OTHER PUBLICATIONS

Written Opinion mailed mailed May 23, 2017 in corresponding PCT International Application No. PCT/SE2017/000014.
G. Lind et al., "Gelatine-embedded electrodes-a novel biocompatible vehicle allowing implantation of highly flexible microelectrodes," Journal of Neural Engineering, vol. 7, 10 pages (2010).

\* cited by examiner

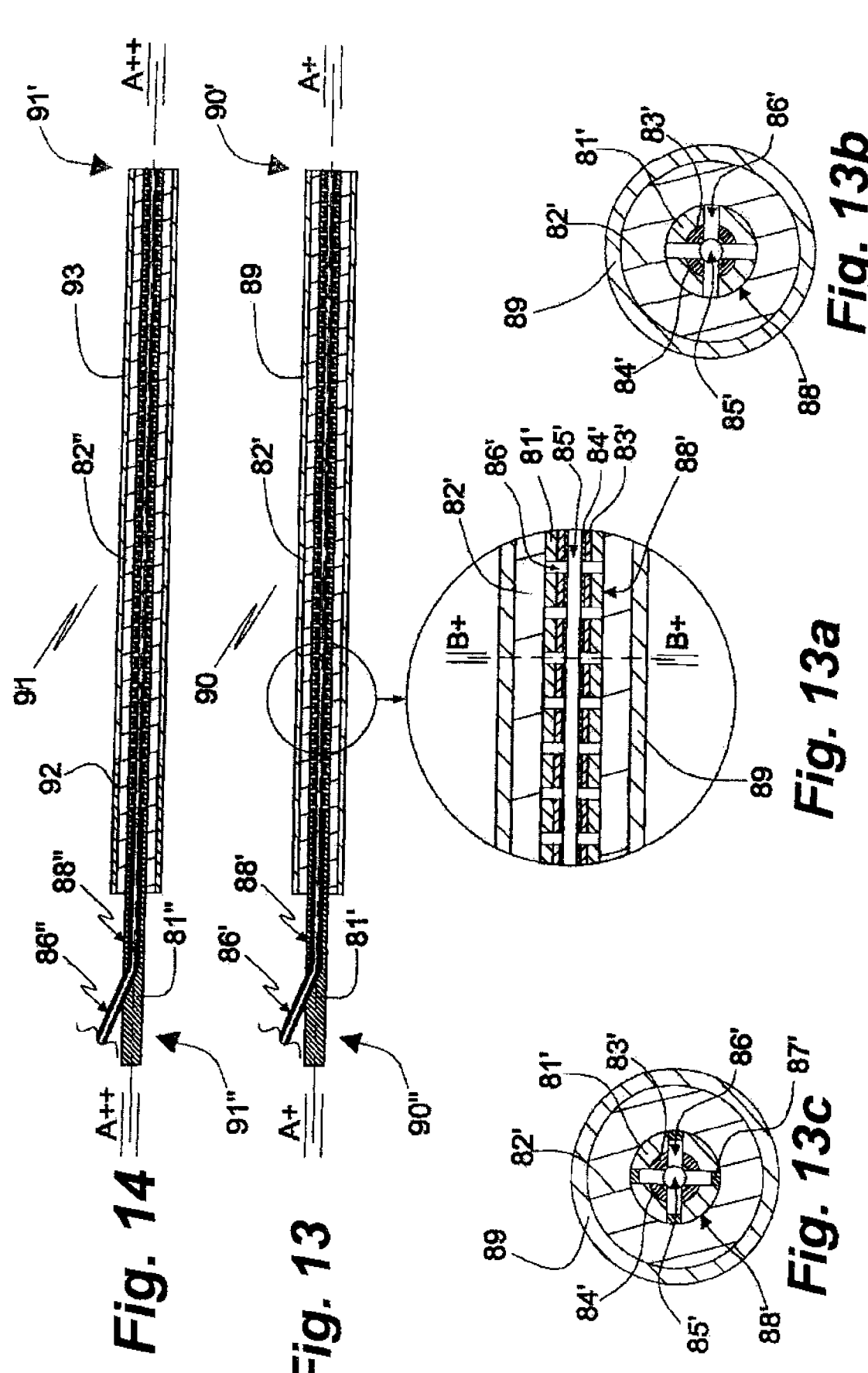

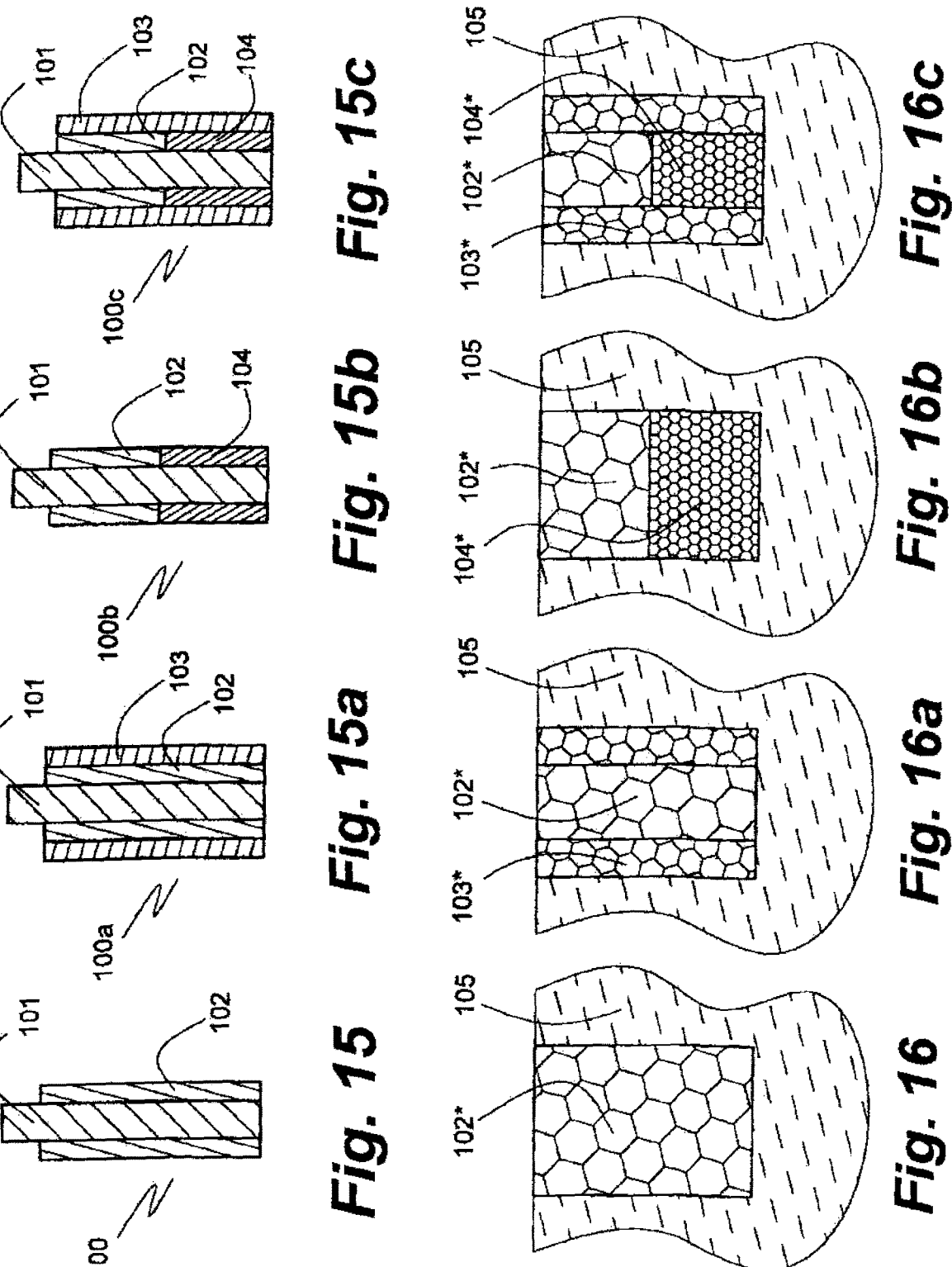

METHOD OF IMPLANTATION OF CELL AGGREGATES AND TISSUE FRAGMENTS

CROSS REFERENCE OF RELATED PATENT APPLICATION

This is a continuation of prior application Ser. No. 16/073,373, filed Jul. 27, 2018, by Jens SCHOUENBORG, now U.S. Pat. No. 11,724,080B2, issued on Aug. 15, 2023, and entitled METHOD OF IMPLANTATION OF CELL AGGREGATES AND TISSUE FRAGMENTS, which is a 35 U.S.C. §§ 371 national phase patent application of PCT/SE2017/000014, filed Feb. 23, 2017, which claims priority to Swedish Patent Application No. 1600070-5, filed Feb. 26, 2016, the contents of which are incorporated by reference herein. The PCT International Application was published in the English language.

FIELD OF THE INVENTION

The present invention relates to a method of implanting living cells in form of cell aggregates or tissue fragments into soft tissue, in particular nervous tissue, of a person or mammal. Furthermore, the present invention relates to a corresponding means, to a method of providing such means, and to an apparatus for use in such provision. The cell aggregates and tissue fragments to which the invention relates are not sufficiently physically stable per se for direct implantation by insertion into the tissue.

BACKGROUND OF THE INVENTION

The implantation of living cells, in particular stem cells, cell aggregates and tiny pieces of tissue obtained by culturing stem cells and other cells into soft tissue, in particular nervous tissue, is problematic. Single cells are at great risk of be damaged during implantation whereas cell aggregates or tissue fragments are at risk of being disintegrated. Another problem consists in how to dispose cells or cell aggregates at a desired tissue location. An additional problem is nervous tissue irritation by foreign material resulting in loss of neurons and proliferation of astrocytes.

OBJECTS OF THE INVENTION

A primary object of the invention is to provide a method of the aforementioned kind that solves one or several problems related to the insertion of living cells, cell aggregates and tissue fragments into soft tissue, in particular neural tissue. Neural tissue comprises brain and spinal cord tissue but also peripheral nerves, dorsal root ganglia, and retina tissue.

Other objects of the invention are to prevent or reduce or stop bleeding along a neural tissue insertion path; to protect neighboring nerve cells from negative effects of such implantation; to the preservation of the capacity of correcting the disposition of implanted cell aggregates and tissue fragments.

Another object of the invention is to provide an apparatus for use in the method.

A further object of the invention is to provide a method of manufacture of apparatus and devices for this kind of implantation.

Additional objects of the invention will become apparent from the following summary of the invention, the description of preferred embodiments thereof illustrated in a drawing, and from the appended claims.

SUMMARY OF THE INVENTION

The present invention is based on the insight that the provision of a channel in neural tissue filled with a biocompatible aqueous gel such as aqueous gelatin gel allows implantation by insertion into soft tissue, in particular neural tissue, of aggregates of living cells and of living tissue, in particular of aggregates of neural cells and neural tissue fragments. It is presumed that such aggregates and tissue fragments are insufficiently physically stable for direct insertion into soft tissue, in particular neural tissue. Neural tissue comprises brain, spinal cord, and endocrine tissue but also peripheral nerve, dorsal root ganglia, retinal, and cochlear tissue. In this application a preferred tissue fragment for implantation is a fragment or sheet of embryonic tissue but also one of tissue engineered in vivo suited for replacing or assisting host tissue, for instance after a stroke.

The present invention is also based on the insight that the host tissue is compromised by the implantation process, generating a hostile environment jeopardizing survival of the implant. It is well known that a large fraction of cells implanted into brain tissue do not survive.

The present invention is furthermore based on the insight that host tissue selected for implantation often is in an inflammatory condition characterized by insufficient blood supply and activated immune cells, such as after a stroke or during degenerative processes.

The linear, preferably cylindrical, channel of the invention in soft tissue, in particular in nervous tissue of a person or animal for implantation an aggregate of living cells or a fragment of living tissue is filled with a gel formed by contact of body fluid with a dry gel forming agent on a substantially rigid, preferably cylindrical pin. Preferred gel forming agents comprise or consist of gelatin, hyaluronic acid and salts thereof, chemically modified gelatin, chemically modified hyaluronic acid and salts thereof. Chemically modified gelatin and chemically modified hyaluronic acid comprise partially hydrolytically degraded gelatin and hyaluronic acid and/or cross-linked gelatin and hyaluronic acid. It is however possible but not preferred for the channel to be of other form than cylindrical; channels of about square or other radial section can be provided by using correspondingly formed pins. A cylindrical channel can comprise two or more cylindrical layers of aqueous gel of same diameter as the channel or a cylindrical central layer of aqueous gel is surrounded by a peripheral layer of aqueous gel. The term "cylindrical channel" comprises cylindrical channels of ellipsoid form in a radial section. The channel of the invention is about straight, that is, deviates less than 10°, in particular less than 5° from a given central axis. The channel has a length that is substantially greater than its width, in particular by a factor of 5 or 10 or 20 and more. The side and bottom (front) walls of the channel are formed by living soft, in particular nervous tissue. For this and other reasons the geometry of the channel may change over time. In particular, the diameter of the channel may shrink over time.

According to the present invention an aggregate of living cells or the fragment of living soft tissue is disposed in the channel of the invention filled with aqueous gel either by adapting the pin covered with dry gel forming agent with a means for such disposition, in particular a means in form of an axially extending passage in the pin, or by providing a separate apparatus for injection of the aggregate of living cells or the fragment of soft tissue in the channel of the invention filled with aqueous gel.

Thus, according to the invention is disclosed such separate apparatus for disposing an aggregate of living cells or a fragment of living soft tissue in a pre-formed channel in soft tissue filled with aqueous gel, the apparatus comprising or consisting of a pipette or syringe of a lumen of constant radial section comprising front and rear openings. According to one aspect of the invention the aggregate or fragment is disposed in the lumen of the pipette or syringe, the pipette or syringe is inserted to a desired depth into the channel with its front end foremost; the aggregate or fragment is expelled from the front opening of the pipette or syringe into the gel; then the pipette or syringe is withdrawn from the gel.

Thus, according to the present invention is disclosed an apparatus for forming a linear channel in soft tissue, in particular nervous tissue, the apparatus being adapted for implantation of an aggregate of living cells or a soft tissue fragment. The apparatus comprises or consists of an oblong rigid pin having a front end and a rear end and a layer comprising or consisting of dry gel forming agent disposed on a pin section extending from the front end in a distal direction and enclosing said section. The layer comprising or consisting of dry gel forming agent contains less than 20% by weight of water, preferably less than 10% by weight, most preferred less than 5% by weight. The pin is sufficiently rigid to allow it to be inserted into the tissue in absence of its layer comprising or consisting of dry gel forming agent. It is preferred for the pin to comprise a passage extending between its front end and its rear end. The passage is preferably circular or elliptic. Alternatively the passage is rectangular, rhomboid or trapezoid or about rectangular, rhomboid or trapezoid in a radial section; in such case it is preferred for a radial width of the passage at a given axial position to be greater by a factor of two or three or five or more than the radial width perpendicular to it. It is preferred for the pin to be cylindrical, elliptic, rectangular, rhomboid or trapezoid or about cylindrical, elliptic, rectangular, rhomboid or trapezoid in a radial section.

The pin is made of a rigid material, in particular of a material as rigid as possible, so as to provide a device of radial dimensions as small as possible to minimize damage to the tissue into which is inserted.

In one aspect of the invention the pin comprises or consists of a metal, a metal alloy or an electrically conducting polymer or other conducting non-metallic material such as carbon, preferred metals being selected from the group consisting of gold, silver, copper, platinum, iridium, titanium, chromium, tungsten, aluminum, and their alloys, any of tungsten, iridium and stainless steel being particularly preferred. This allows the pin to be additionally used as an electrode. In such case an electrically conducting lead is attached to or near the rear end of the pin in an electrically conducting fashion. The lead establishes electrical communication of the pin with, for instance, a voltage monitoring device or a source of electric power.

In another aspect of the invention the pin is of a non-conducting material, in particular a polymer material suitable for providing sufficient stiffness, such as polycarbonate, polystyrene, polyvinylchloride, and polyacrylate. The pin may consist of or be covered by a material facilitating withdrawal upon formation of the aqueous gel. Parylene C, silicon rubber and Teflon® are materials particularly useful for this purpose.

According to a particularly preferred aspect of the invention the apparatus comprises a tubiform insertion guide having frontal and distal ends, wherein the rigid pin is disposed. The pin covered with the layer consisting of or comprising dry gel forming agent comprises distal, central and proximal portions, wherein the central portion is of same diameter, the distal portion is of a diameter smaller than that of the central portion and decreasing towards its distal end, and the proximal portion is of same diameter as the central portion or of a larger diameter, wherein the lumen of the insertion guide in a radial section is of same form as a radial section of the central portion but slightly larger so as to allow the central portion of the pin to be displaced slidingly within the guide, and wherein the guide comprises a means for immobilizing it in respect to the tissue into which the pin is inserted. According to a preferred embodiment the tubiform insertion guide comprises a flange or sleeve radially extending from its distal end. The insertion guide is mountable on the rigid pin covered with the layer consisting of or comprising dry gel forming agent in the same distal/proximal orientation as that of the pin. According to another preferred embodiment the insertion guide comprises a rigid mounting element attached to a tubiform portion thereof or to the sleeve, the mounting element being attachable at its other end directly or indirectly to the person or animal to which the tissue belongs.

According to another preferred aspect of the invention the apparatus, in particular the pin, comprises one or more means selected from electrode means, optical fiber means, sensor means.

It is preferred for the axially extending passage of the pin to be plugged at its distal opening by a plug which is dissolvable or degradable in aqueous body fluid, such as by one consisting of or comprising dry gel forming agent, which gel forming agent is capable of forming a gel in contact with aqueous body fluid.

The dry gel forming agent of the invention is biocompatible, In particular, it is an agent selected from the group consisting of gel-forming protein, gel-forming carbohydrate, gel-forming glycoprotein, and combinations thereof. It is preferred for the gel-forming protein to be selected from a biocompatible proteinaceous gel forming agent, in particular an agent selected from the group consisting of gelatin, hyaluronic acid, chemically modified gelatin, recombinant gelatin, chemically modified hyaluronic acid, recombinant hyaluronic acid, and salts thereof. The biocompatible gel prevents shrinkage of the channel radially inwardly and thus stabilizes the geometry of the channel, at least for a period of time during which the gel is not substantially altered, that is, weakened by enzymatic degradation or otherwise. The use of cross-linked gels may extend the time of substantially stabilized geometry, which can be tailored by the extent of crosslinking.

The biocompatible gel formed by contact of dry gel forming agent with aqueous body fluid allows tiny aggregates of living cells and fragments of living soft tissue to be inserted into it, in particular slowly inserted into it, without substantially affecting their geometry. A slow rate of insertion is a rate of up to 5 mm per second, in particular of 1 or 2 mm per second. This is in stark contrast to the resistance of soft tissue, in particular nervous tissue, to such insertion. Typically, the resistance of an aqueous gel of the invention is lower by a factor of 10 or more, in particular by a factor of 25 or more than the resistance of neural tissue, in particular the meningeus and other fibrous membrane layers. A measure of the resistance against penetration is the time required for an oblong pin of given dimensions to penetrate to a defined depth under the influence of a constant force acting on the pin in an axial distal direction.

The biocompatible gel of the invention is translucent, which is particularly advantageous for the use of visible and near IR radiation emitted through an optical fiber disposed in the channel.

A preferred aspect of the present invention is based on the additional insight that the formation of aqueous biocompatible gel, in particular of aqueous gelatin gel, in the channel can have neuroprotective effect comprising reduction of microglia response to medical devices implanted into neural tissue.

According to the present invention gelatin from various animal sources can be used as a gel forming agent, such as bovine, pig skin, poultry skin, and tuna gelatin. Gelatin from mammal sources is preferred due to its superior gelling capacity at body temperature. Recombinant gelatin may also be used. For forming a channel of extended stability the use of chemically cross-linked gelatin is preferred due to its slower rate of degradation in the body. Examples of efficient gelatin cross linking agents are bis(vinylsulfonyl)methane and 1-ethyl-3(3-dimethylamino-propyl)carbodiimide. Another useful crosslinking method is by UV radiation. The rate of degradation in the body can be controlled by the extent of cross-linking, which in turn can be controlled by the amount of cross-linking agent used or by controlling the exposure to UV radiation used for cross-linking a given amount of gelatin.

Other aqueous biocompatible gels of the invention include carbohydrate gels.

Carbohydrate gels useful in the invention include arabinogalactan gel, arabinoxylan gel, galactan gel, galactomannan gel, lichenan gel, xylan gel but also cellulose derivatives such as hydroxymethylpropyl cellulose, and are formed by contact with aqueous media, in particular aqueous body fluid, with a gel forming agent selected from: arabinogalactan, arabinoxylan, galactan, galactomannan, licenan, xylan, hydroxymethyl cellulose and other cellulose derivatives forming gels in contact with aqueous media.

Further aqueous biocompatible gels of the invention include protein gels. Protein gels other than gelatin from animal sources useful in the invention include whey protein gel, soy protein gel, casein gel, which are formed by contact of aqueous media, in particular aqueous body fluid with a gel forming agent selected from whey protein, soy protein, casein.

Still other aqueous gels for use in the invention can be formed by contact of aqueous media, in particular aqueous body fluid, with a gel forming agent selected from the group consisting of: arabinogalactan; arabinoxylan; galactan; galactomannan; lichenan; xylan; cellulose derivatives such as hydroxymethylpropyl cellulose; whey protein; soy protein; casein; hyaluronic acid; chitosan; gum Arabic; carboxyvinyl polymer; sodium polyacrylate; carboxymethyl cellulose; sodium carboxymethyl cellulose; pullulan; polyvinylpyrrolidone; karaya gum; pectin; xanthane gum; tragacanth; alginic acid; polyoxymethylene; polyimide; polyether; chitin; poly-glycolic acid; poly-lactic acid; co-polymer of poly-glycolic and poly-lactic acid; co-polymer of poly-lactic acid and polyethylene oxide; polyamide; polyanhydride; polycaprolactone; maleic anhydride copolymer; poly-hydroxybutyrate co-polymer; poly(1,3-bis(p-carbophenoxy)propane anhydride); polymer formed by co-polymerization with sebacic acid or with poly-terephthalic acid; poly(glycolide-co-trimethylene carbonate); polyethylene glycol; polydioxanone; polypropylene fumarate; poly(ethyl glutamate-co-glutamic acid); poly(tert-butyloxy carbonylmethyl glutamate); poly-caprolactone; poly(caprolactone-co-butylacrylate); poly-hydroxybutyrate and copolymers thereof; poly(phosphazene); poly(D,L-lactide-co-caprolactone); poly(glycolide-co-caprolactone); poly(phosphate ester); poly(amino acid); poly(hydroxybutyrate); polydepsidpeptide; maleic anhydride copolymer; polyphosphazene; polyiminocarbonate; poly[(7.5% dimethyl-trimethylene carbonate)-co-(2.5% trimethlyene carbonate)]; polyethylene oxide; hydroxypropylmethylcellulose, poly(ethylene-co-vinyl acetate); isobutylene-based copolymer of isobutylene and at least one other repeating unit such as butyl acrylate: butyl methacrylate; substituted styrene such as amino styrene, hydroxy styrene, carboxy styrene, sulfonated styrene; homopolymer of polyvinyl alcohol; co-polymer of polyvinyl alcohol and at least one other repeating unit such as a vinyl cyclohexyl ether; hydroxymethyl methacrylate; hydroxyl- or amino-terminated polyethylene glycol; acrylate-based copolymer such as methacrylic acid, methacrylamide, hydroxymethyl methacrylate; ethylene vinyl alcohol copolymer; silicone based copolymer of aryl or alkyl siloxane and at least one repeating unit; polyurethane; heparan sulfate; RGD peptide; polyethylene oxide; chrondroitin sulfate; YIGSR peptides; keratan sulfate; VEGF biomimetic peptide; perlecan (heparan sulfate proteoglycan 2); Ile-Lys-Val-Ala-Val (IKVAV) containing laminin alpha-1 chain peptide; modified heparin; fibrin fragments, According to a preferred aspect of the invention the gel-forming layer comprises a pharmacologically active agent, in particular one selected from the group consisting of coagulant, anticoagulant, antibiotic, osmotic pressure adjusting agent, anti-inflammatory agent, nutrient, factor stimulating growth, factor stimulating cell differentiation, hormone, immunosuppressive agent.

According to the present invention is also disclosed a method for implantation of an aggregate of living cells or a soft tissue fragment, in particular a fragment of embryonic tissue, into neural tissue, comprising: providing a channel in the tissue filled with aqueous gel, the channel optionally comprising a pin comprising an axial passage having open distal front and rear ends disposed therein; optionally providing one of: syringe comprising a plunger and pipette; loading the syringe or pipette or the passage with the aggregate or fragment; optionally inserting the syringe needle or pipette into the gel; expelling the aggregate or fragment from the syringe or pipette or passage into the gel; optionally withdrawing the syringe needle or pipette from the gel. A time difference between provision of the channel and implantation is optionally at least a few minutes, in particular at least one or two or six hours, and even at least one or two or five days.

According one preferred aspect of the invention the aggregate or fragment is comprised by a support, in particular a support selected from matrix comprising open channels and sheet of solid material. The matrix preferably comprises or consists of fibrous material, in particular a fibrous material that is dissolvable or biodegradable in aqueous body fluid. The fibrous material optionally comprises fibers comprising or consisting of native and/or recombinant and/or cross-linked gelatin. It is also preferred for the fibers to comprise or consist of one or more components selected from the group consisting of: arabinogalactan gel, arabinoxylan gel, galactan gel, galactomannan gel, lichenan gel, xylan gel cellulose derivatives such as hydroxymethylpropyl cellulose; gel forming protein such as whey protein, soy protein, casein; hyaluronic acid. According to another preferred aspect of the invention the sheet of solid material is dissolvable or biodegradable in aqueous body fluid. Native and/or recombinant and/or cross-linked gelatin is a preferred sheet material. Other preferred sheet materials are arabinogalactan gel, arabinoxylan gel, galactan gel, galactomannan gel, lichenan gel, xylan gel cellulose derivatives such as hydroxymethylpropyl cellulose; gel forming protein such as whey protein, soy protein, casein; hyaluronic acid.

According to a still further advantageous aspect of the invention the lumen of the syringe needle or pipette or of the passage of the pin used in the method is of non-circular form in a radial section.

According to the present invention is disclosed a combination of the syringe or pipette of the invention, in particular in a form loaded with an aggregate of living cells or a fragment of living soft tissue, and an insertion guide for keeping the syringe or pipetted in a desired radial disposition in respect to the channel in soft tissue filled with aqueous gel during the injection of the cell aggregate or tissue fragment into the channel. The insertion guide comprises a tube having frontal and distal ends into the lumen of which the pipette or syringe can be inserted and slidingly displaced in both axial directions. To this effect a radial section the lumen of the tube is slightly larger than a radial section of the pipette. It is preferred for the insertion guide to comprise a radially extending flange mounted at the distal end thereof. It is furthermore preferred for the insertion guide to comprise a rigid holding element attached at its one end to the tube and/or the flange of the insertion guide and, at its other end, attachable, directly or indirectly, to the person or animal provided with the channel so as to immobilize the combination in respect of the person or animal.

According to another preferred aspect of the invention the syringe or pipette is loaded with a support comprising an aggregate of living cells or a soft tissue fragment, in particular an embryonic tissue fragment, wherein the support is selected from the group consisting of: matrix with open pores, sheet of solid material and combinations thereof. The matrix preferably comprises or consists of a fibrous material, in particular a fibrous material selected from the group consisting of: native gelatin; cross-linked gelatin; arabinogalactan; arabinoxylan; galactan; galactomannan; lichenan; xylan; cellulose derivatives such as hydroxymethylpropyl cellulose; gel forming protein such as whey protein, soy protein, casein; hyaluronic acid.

According to a preferred aspect is disclosed a syringe or pipette of the invention loaded with living cells or aggregates of living cells disposed in a matrix with open pores, in particular a matrix comprising or consisting of biocompatible fiber, in particular a fiber that is soluble or biodegradable in body fluid.

According to another preferred aspect of the invention is disclosed a system comprising an aggregate of living cells or a soft tissue fragment comprising living cells physically supported by any of: sheet or disc of biocompatible material, biocompatible fiber, and combinations thereof;

wherein the sheet is of a material that is biodegradable or soluble in aqueous body fluid;

wherein the sheet is of a size from about 0.5 mm to 1.0 mm or more, such as up to 2 mm or 3 mm or 5 mm or more, exceptionally up to 25 mm and more. The supporting sheet can be of any suitable form, such as rectangular and elliptic. Size of the sheet means its maximum width. It is preferred for the physically supported aggregate or fragment to comprise biocompatible fiber enclosing said aggregate or tissue disposed on said sheet in a manner forming a non-woven web comprising open pores. Particularly preferred is a support comprising a fibrous matrix of gelatin or other biocompatible polymer, including polymers of this kind that have been chemically and/or physically modified, such as by cross-linking. A biocompatible fiber of the aggregate or sheet other than of gelatin is preferably one selected from the group consisting of: arabinogalactan; arabinoxylan; galactan; galactomannan; lichenan; xylan; cellulose derivatives such as hydroxymethylpropyl cellulose; gel forming protein such as whey protein, soy protein, casein; hyaluronic acid.

According to a further preferred aspect of the invention the solid support comprises microelectrode and/or optical fiber means for guiding insertion in the channel filled with gel to provide for desired disposition of the support in the tissue. In such case it is preferred for the aggregate of living cells or the soft tissue fragment to substantially consisting of a non-woven web enclosing said cell aggregate or tissue fragment and one or both of microelectrode and optical fiber of which at least one is attached to the web in a non-releaseable manner; it is preferred for the biocompatible fiber to enclose a portion of the microelectrode and/or the optical fiber.

According to an additional preferred aspect of the invention the support comprises two or more teeth protruding laterally from the support sheet for co-operation with two or more axially extending guidance slots disposed in the lumen of a syringe needle or a pipette so as to limit the radial displacement but not the axial displacement of the aggregate or fragment upon its disposition in the lumen.

The invention will now be explained in greater detail by reference to a number of preferred embodiments illustrated in a rough drawing, which is not to scale. Radial dimensions are greatly exaggerated. All figures are axial or radial sections.

BRIEF DESCRIPTION OF THE DRAWINGS

FIG. 3 illustrates an aggregate of cells of invention disposed in a fibrous matrix, in a side view;

FIG. 4 illustrates the aggregate of FIG. 3 disposed in a syringe, in axial section, and a partial enlargement thereof;

FIG. 5 illustrates a single-layer aggregate of cells cultured on a solid support attached at its rear end to a releasable insertion guide of which only the distal portion is shown, in a side view;

FIG. 5a is a transverse section P-P of the aggregate of FIG. 5;

FIG. 6 illustrates the aggregate of FIGS. 5, 5a disposed in the about rectangular lumen of a syringe or pipette of about rectangular form, in a radial section and in the same view as in FIG. 5a;

FIG. 7 illustrates the aggregate of FIGS. 5, 5a disposed in the lumen of a syringe or pipette of about elliptic form in a radial section, in the same view as in FIG. 5a, the support comprising an axially extending optical fiber or microelectrode;

FIG. 8 illustrates a variety of the aggregate of FIGS. 5, 5a provided with an axially extending conductor for electricity or radiation, disposed in the lumen of a syringe or pipette of ellipsoid form in radial section, in the same view as in FIG. 5a;

FIG. 7a showing an enlarged portion thereof) section, the apparatus comprising, in addition to a cylindrical pin covered with dry gelatin and comprising optical fiber and electrode means, an axially extending passage in the pin for injection of fluid material into the channel from the opening of the passage at the distal face of the apparatus;

FIGS. 13-13c illustrate an apparatus according to the invention corresponding to that of FIGS. 12-12c, provided with a layer of friction reducing agent on the gelatin layer;

FIG. 14 illustrates a variety of the apparatus of FIG. 13 and in the same section, the gelatin layer being covered by a first, friction reducing layer extending from the distal end of the pin in a proximal direction and by a second layer comprising anticoagulant extending from the proximal end of the friction reducing layer in a proximal direction;

FIGS. 15-15c illustrate four embodiments of cylindrical pins of the invention covered with one or more layers of dry gel forming agent used in the production of corresponding cylindrical channels in nervous tissue filled with aqueous gel, in an axial (channel axis) section;

FIGS. 16-16c illustrate four embodiments of the cylindrical channel of the invention in nervous tissue of filled with one or more layers of aqueous gel, produced by implantation of the pins of FIGS. 11, 11a, 11b, 11c, respectively, in an axial (channel axis) section.

DESCRIPTION OF PREFERRED EMBODIMENTS

Figures 1, 1G, 1H, 4A:
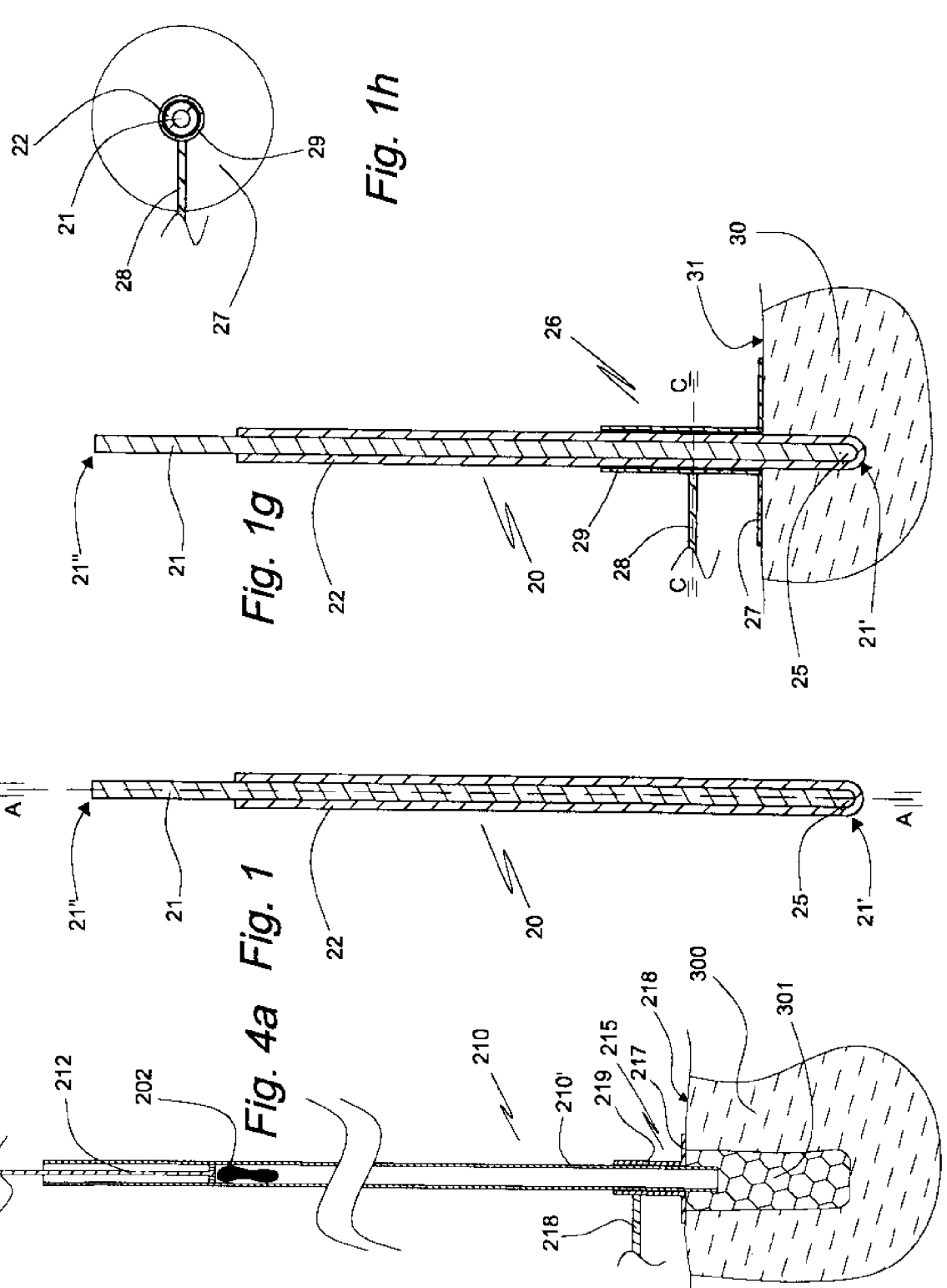
FIG. 1 shows an apparatus of the invention for forming a channel in soft tissue, in particular nervous tissue, in an axial section A-A.
FIGS. 1g; 1h illustrate an apparatus of the invention mounted in an insertion guide, in the same view as in FIG. 1 (FIG. 1g) and in a radial section (FIG. 1h) disposed on a body surface and in the course of being inserted into soft tissue.
FIG. 4a illustrates the syringe of FIG. 3 comprising an aggregate of cells mounted at a channel in soft tissue filled with aqueous gel by means of an insertion guide, in an axial section.
Figures 1A, 2C:
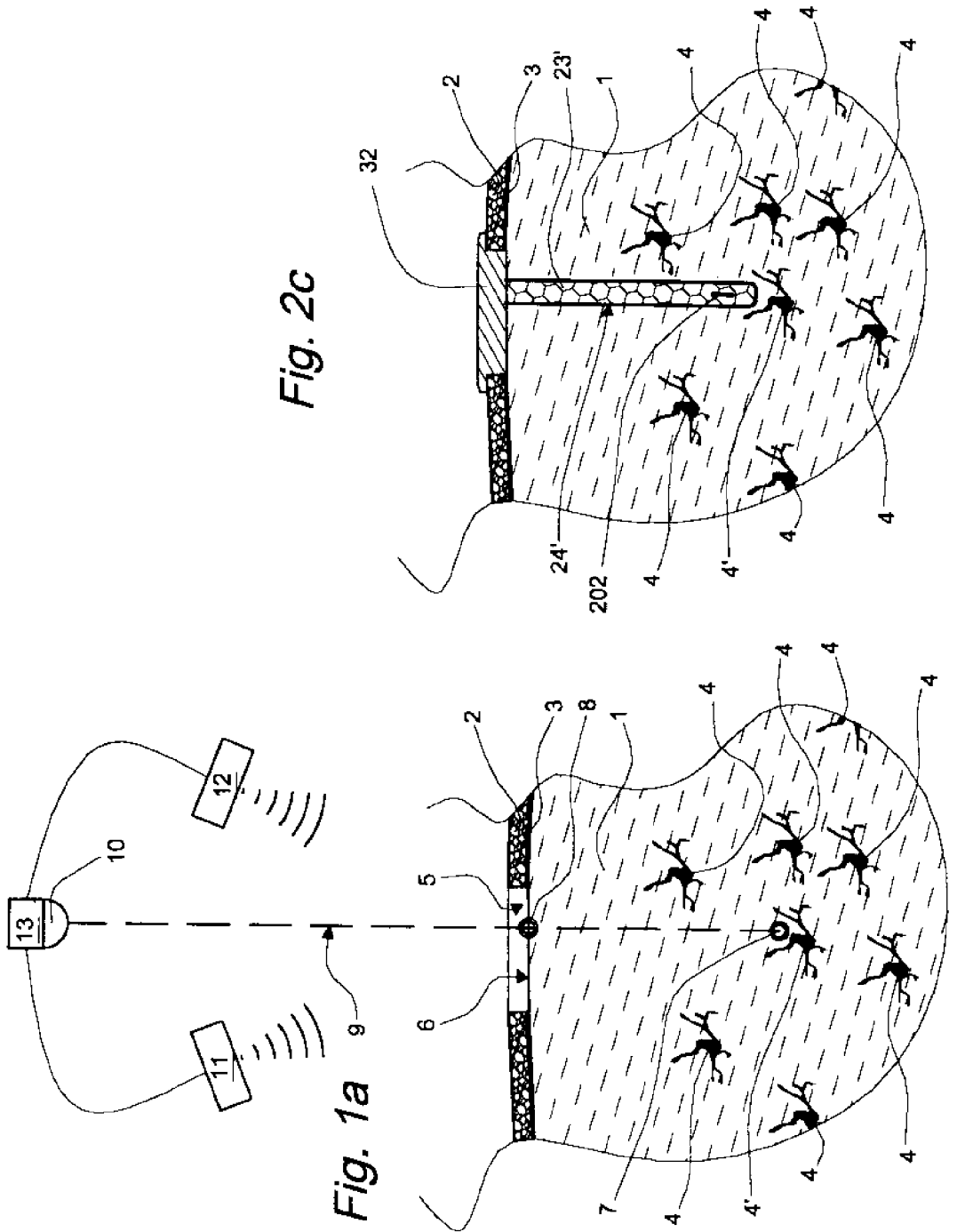
FIGS. 1a-1f illustrate the method of the invention for providing a channel in nervous tissue of a person or a mammal for implantation of an aggregate of living cells or a fragment of living tissue and a channel (FIG. 1e) so produced, the method including identification of the position of a target in the nervous tissue in respect of which the front end of the channel is desired to be disposed.
FIGS. 2a-2c illustrate the method of the invention for implanting an aggregate of living cells into nervous tissue by inserting it into the channel of FIG. 1e, and an aggregate so implanted (FIG. 2c)

Example 1. Determination of Position of Target, Front (Bottom) End of Channel, Rear (Top or Open) End of Channel, Providing Guiding Information for Insertion of Channel-Forming Apparatus FIG. 1a is a rough representation of a section of a mammal brain 1 with adjacent portions of skull bone 2 and dura mater 3. A through bore 5 has been provided in the skull bone 2 through which a face 6 of the brain tissue 1 can be accessed after removal of a portion of the dura mater 3. In the brain tissue 1 a number of neural cells or rather cell clusters comprising 100 or more cells 4 are shown. One of them 4' has been identified as a desired target for nervous cell potential with a microelectrode. The location of the target neural cell/cell cluster 4' is determined by employing a combination of two imaging systems such as Computer Tomography (CT) 11 and Magnetic Resonance Imaging (MRI) 12 electrically connected with and controlled by a control unit 13. Based on the location information a microprocessor of the control unit 13 determines an insertion track 9 for a channel forming apparatus 20 (FIG. 1), which is visualized by a laser 10 beam controlled by the control unit 13. The control unit 13 additionally determines a point 7 on the track near the target neural cell 4' cluster corresponding to the distal end of a channel (23', FIG. 1c) to be formed so as to define the insertion depth of the channel forming apparatus 20 (FIG. 1). The point 8 on the insertion track 9 where the laser beam hits the free face 6 of the brain tissue 4 is also determined. Point 8 represents the point of insertion into brain tissue 1 of the channel forming apparatus 20 (FIG. 1).

Example 2. First Embodiment of a Channel-Forming Apparatus of the Invention and Manufacture Thereof An embodiment of the channel forming apparatus 20 of the invention is shown in FIG. 1 in axial section A-A. The channel forming apparatus 20 comprises a stiff cylindrical pin 21 of a rigid material and a layer 22 of gelatin on a portion of the pin 21 extending from its front (distal) end 21' in the direction of its rear (proximal) end 21". The layer of gelatin 22 can be substituted by a corresponding layer of another agent capable of forming a gel on contact with body such as hyaluronic acid or PEG or a combination of such agents. The axial extension of the layer 22 corresponds to at least the depth of the channel to be formed. The diameter of the pin 21 is smaller than the diameter of the channel to be formed and should be kept as small as possible. The thickness of the layer 22 on the pin is determined by the desired width of the channel to be formed. To reduce tissue damage during implantation the pin 21 should be tapering towards its distal end, such as by ending in a sharp or rounded tip 25, in particular a conically rounded tip. The material of the pin 21 is not critical but should provide good adherence for the layer of 22 of gelatin or other agent capable of forming a gel on contact with aqueous body fluid. On the other hand, the material of the pin or a material covering the surface of the pin should easily release the aqueous gel formed upon contact of the dry gel forming agent with aqueous body fluid, that is, should not provide good adherence for the so formed aqueous gel. The use of a poly-fluorinated material such as Teflon® covering the pin 21 constitutes an acceptable compromise. Other useful materials include silicones of various kind. Useful pin 21 materials include steel, aluminum, polycarbonate, polyester, glass, ceramics but also titanium, gold, platinum and alloys thereof. They may be covered by, for instance, a thin layer of poly-fluorinated material or a silicone or their surface may be silanized.

In FIGS. 1g, 1h the apparatus 20 of FIG. 1 is shown mounted in an insertion guide 26 comprising a tube element 29 of a slightly larger inner diameter (lumen) than the outer diameter of the apparatus 20, that is, of the diameter of the pin 21 covered with gel forming agent 22. At its distal end the tube element 29 has radially extending flange 27 mounted to its cylindrical outer face. The function of the flange 27 is to abut the surface 31 of the tissue 30 into which the apparatus 20 is desired to be inserted, thereby stabilizing the manipulation of the apparatus 20. For further stabilization of the apparatus 20 during insertion into soft tissue the insertion guide 26 comprises a radially extending holding element 28 fastened to the cylindrical outer face of the tube element 29 at a distance from the flange 27 in a proximal direction. Via its holding element 28 the insertion guide 26 can be positionally secured in a manner so as to be kept in place, for instance by firm connection with a support (not shown) on which the person or animal to be treated is immobilized.

The channel forming apparatus 20 can be manufactured, for instance, by providing an aqueous solution of gelatin and a pin 21 of stainless steel. The viscosity of the gelatin solution is controlled by temperature and concentration so as to make it visibly viscous but not gelling. The pin 21 is dipped into the gelatin solution, then withdrawn, disposed horizontally, and rotated. Drying of the gelatin solution on the pin 21 can be accelerated by applying heat and/or vacuum. Another factor requiring control is the relative humidity of the manufacturing environment.

The dipping step is repeated until a gelatin layer 22 of desired thickness has been formed on the pin 21. To avoid dissolution of dry gelatin the pin 21 is quickly withdrawn from the gelatin solution.

In another method of manufacture of the channel forming apparatus gelatin or other agent capable of forming a gel on contact with water is applied to the pin 21 by spraying with a corresponding aqueous solution.

In still another method of manufacture of the channel forming apparatus a mould of desired form is used for the manufactures of the channel forming apparatus. In a preferred embodiment two sheets of acrylic material (Plexiglass®) each comprising a hemi-cylindrical moulding section of same size constituting a cylindrical or ellipsoid mould are mounted in an abutting disposition with their axes aligned around a cylindrical pin of the invention, the axis of which is centered in the mould. The sheets are kept in the abutting disposition by a number of screws disposed peripherally of the mould. The radial dimension(s) of the mould is slightly larger than that of the pin. At one axial end of the mould a channel is provided through which a concentrated aqueous solution of the gel forming agent is injected into the space between the pin and the mould walls. Injection is made at a temperature at which the solution is not gelled. The sheets of the mould then are slowly released by loosening the screws to provide access of air for drying. After drying to a water content of about 2% by weight the pin covered with dry gelling agent is removed from the mould. The gelling agent can in turn be coated with a material such as Kollikoat® retarding contact of the dry gelling agent with aqueous body fluid and thus the onset of gelling as well as the end thereof.

Example 3. Forming an Implantation Channel

A preferred embodiment of the process of forming an implantation channel of the invention is shown in FIGS. 1b through 1f.

Figure 1C:
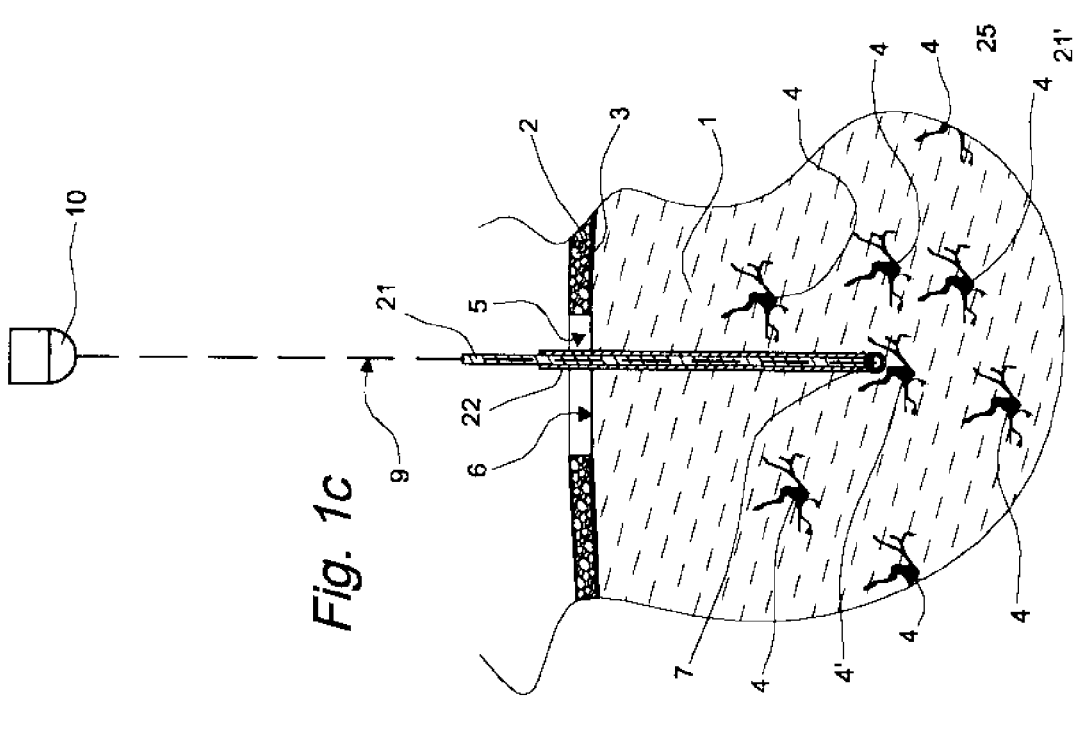
Figure 1B:
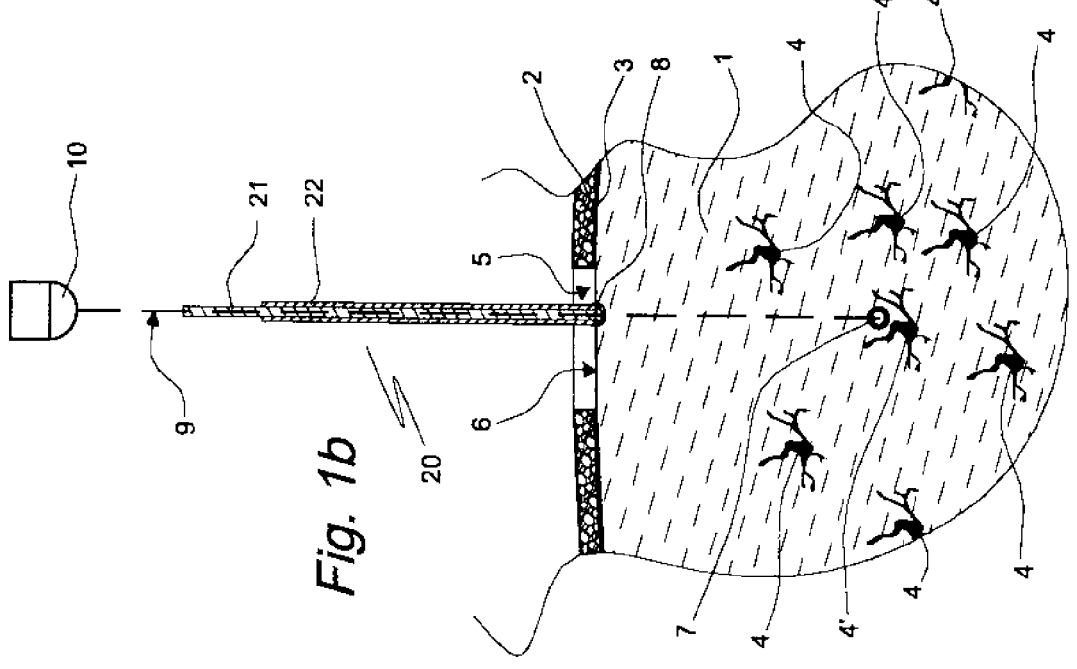
Figures 1D, 1E, 1F:
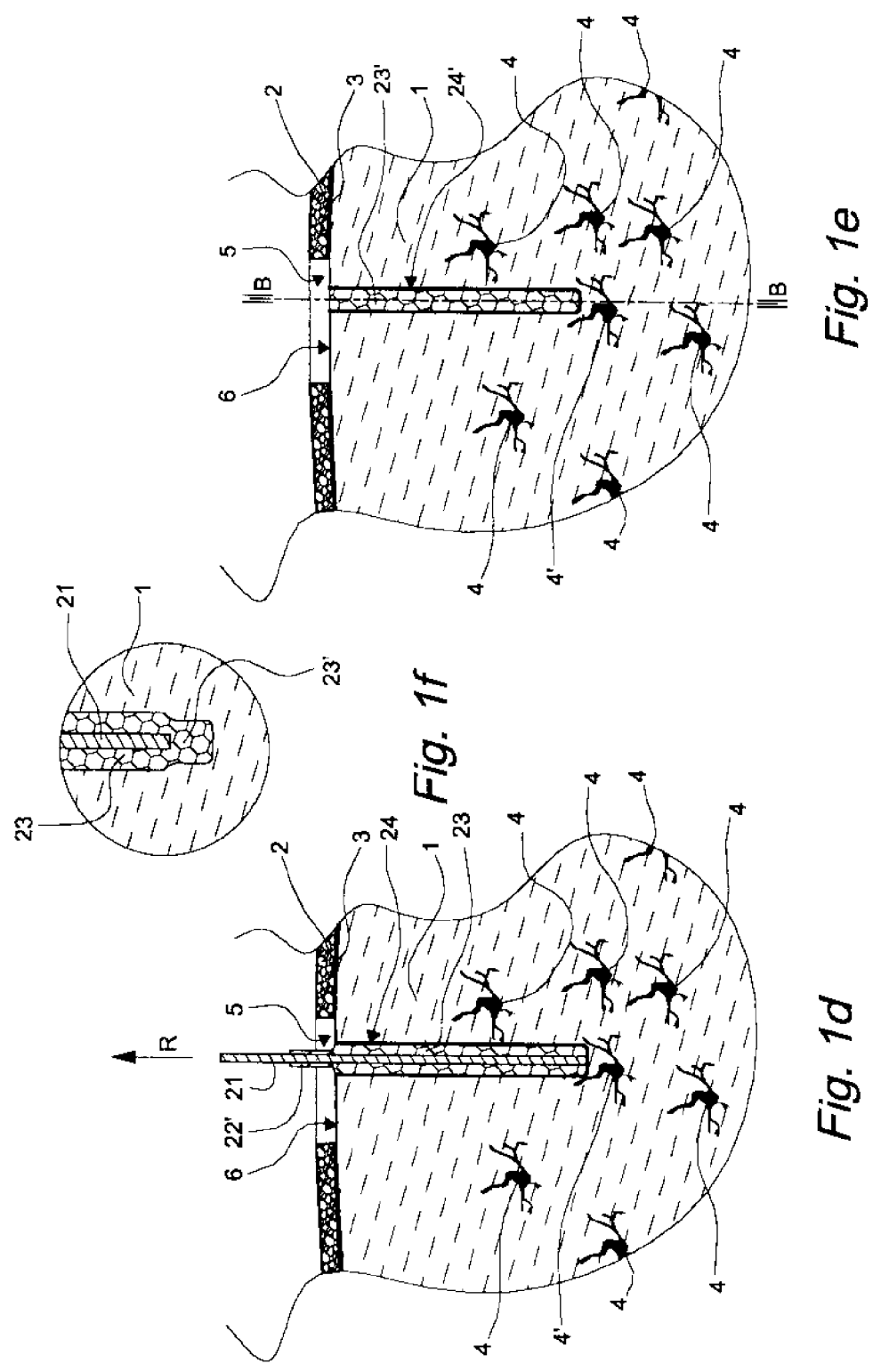

A channel-forming apparatus 20 (FIG. 1) of the invention is positioned with its front end 21' at insertion point 8 on the accessible brain tissue 4 surface 6 and with its axis A-A aligned with the insertion track line 9 (FIG. 1b). The apparatus 20 is then inserted into the tissue 4 along the track line 9 by applying pressure on its rear section lacking a gelatin layer 22. Application of pressure and insertion may be manually or by using an appropriate micromanipulator (not shown). The apparatus 20 is inserted into the desired depth, that is, until its front end has reached the front end 7 of the insertion track or path (FIG. 1c). Insertion should be as fast as possible to avoid dissolution of gelatin in the layer 22 by aqueous body fluid during insertion. Upon full insertion the apparatus 20 is left in the fully inserted position (FIG. 1c) until the gelatin layer 22 has been fully dissolved by aqueous body fluid and a tubiform layer of gelatin gel 23 formed around the pin 21 (FIG. 1d). The combination of pin 21 and tubiform layer of gelatin gel 23 constitute a prechannel visualized in FIG. 1d by its contour 24. Since the axial length of the gelatin layer 22 exceeded the depth of insertion and thus the axial extension of its contact with aqueous body fluid, a proximal terminal portion 22' of the gelatin layer 22 was not dissolved. Non-dissolved gelatin 22' can be dissolved prior to withdrawal of the pin 20 by flushing with saline or artificial cerebrospinal fluid; by this removal adherence of gel from the channel during withdrawal of the pin 20 and thus disturbance of the gel 23 in the channel is prevented.

In the following step the pin 21 is withdrawn (direction R) from the gel 23 along the insertion path 9. Withdrawal of the pin 21 reduces the volume of the pre-channel by the volume of the pin 21 so as to form a channel of the invention visualized in FIG. 1e by its contour 24'. FIG. 1f (enlarged) illustrates an initial phase of withdrawal of pin 21 in which a distal terminal portion of the gelatin gel 23' has shrunken to the diameter of the channel 24' and adopted cylindrical form while the adjacent portion of the gelatin gel 23 is still tubiform. Upon full withdrawal an implantation channel 24 filled with gelatin gel 23' has been formed (FIG. 1e). The amount of gelatin for forming channel 24 can be reduced when using a physically stabilized microelectrode comprising a matrix dissolvable or degradable in aqueous body fluid.

By using cross-linked gelatin or other cross-linked gelforming agent, it is possible to retain upon withdrawal of the pin a channel in the tissue filled with aqueous body fluid. The channel is surrounded by a cylindrical wall of crosslinked gel. It is particular useful for insertion of a not physically stabilized microelectrode or other probe or sensor of the invention into soft tissue.

Figures 9, 10:
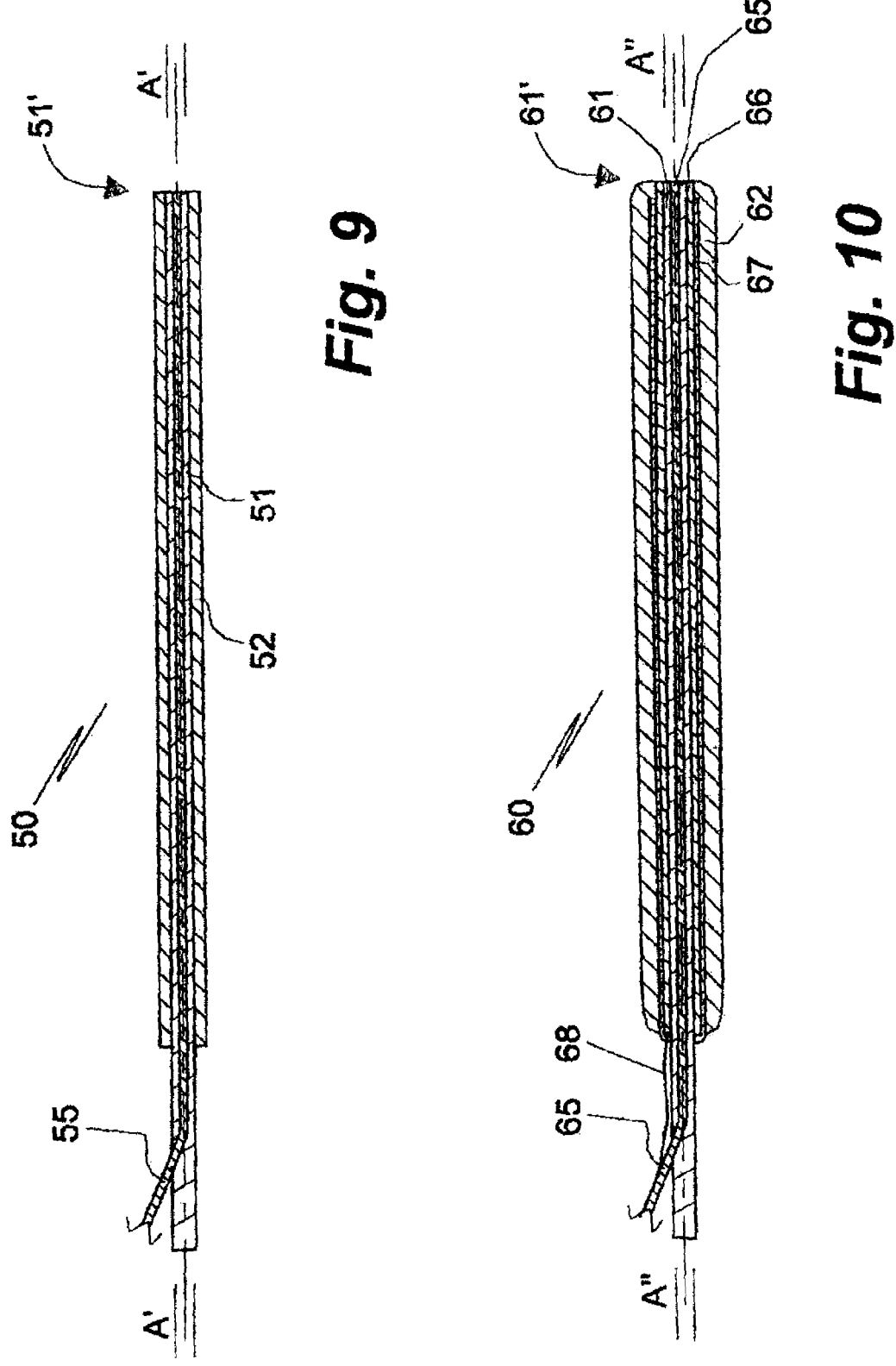
FIG. 9 illustrates an apparatus according to the invention for forming a channel in nervous tissue filled with aqueous gel, the apparatus comprising an optical fiber.
FIG. 10 illustrates an apparatus according to the invention for forming a channel in nervous tissue filled with aqueous gel, the apparatus comprising an optical fiber and a microelectrode.

Example 4. Second Embodiment of the Apparatus According to the Invention Additionally Comprising Optical Fiber Means A second embodiment 50 of the apparatus according to the invention is shown in FIG. 9. Its pin 51 of polyacrylate encloses a centered (axis A'-A') optical fiber 55 extending from the front end 51' of the pin in a proximal direction leaving the pin near the other end thereof so as to emerge in a skew angle from the cylinder wall of the pin. Alternatively, the optical fiber may extend through the entire pin in a centered disposition and leave the pin at its proximal end.

The side wall of the pin 51 is covered by a layer 51 of dry gelatin extending from the distal end 51' to a position distally of where the optical fiber 55 emerges from the cylinder wall. The front end face of the pin 51 is not covered by gelatin. This allows radiation to emerge from the front end of the optical fiber 55 unimpeded and/or inspection of tissue disposed in front of the pin's 51 front end.

Example 5. Third Embodiment of the Apparatus According to the Invention, Additionally Comprising Optical Fiber and Electrode Means A third embodiment 60 of the apparatus of the invention is shown in FIG. 10. It is a modification of the second embodiment in that it further comprises an electrode function. The electrode function is provided by a conductive layer 66 of gold on the pin 61, which encloses an optical fiber 65 disposed centrally and which shares its central axis with that (A"-A") of the pin 61. Except for a short portion near its distal end the gold layer 66 is electrically insulated by a lacquer 67. The gold layer 66 is electrically connected with a control unit (not shown) by an insulated lead 68 attached to the gold layer 66 at the proximal end thereof. A layer 62 of dry gelatin covers insulated and non-insulated portions of the gold layer 66.

Example 6. Physically Supported Cell Aggregates and Tissue Fragments

Physically supported cell aggregates suitable for implantation by the method of the invention are known from, i.a., US 2014/0024117 A1, EP 2388022 A1, US 2002/0064875 A1, US 2004/0101518 A1, US 2004/0266000 A1, US 2005/0226856 A1, US 2006/0141000 A1, US 2007/0048292 A1, US 2009/0060969 A1, US 2010/0041146 A1, US 2010/0297208 A1, US 2012/0045487 A1, US 2014/0112894 A1, incorporated herein by reference. Fibrous supports of this kind can also be used to physically stabilize fragments of living soft tissue by embedding a tissue fragment in a woven or non-woven web of biocompatible fibers disclosed therein.

Thus, supported cell aggregates or soft tissue fragments are of a size allowing their implantation by the method of the invention; their size thus extends from less than 1 mm, such as 0.5 mm, to 5 mm or 10 mm, and exceptionally up to about 25 mm.

Figures 3, 4, 5, 5A, 6, 7, 8:
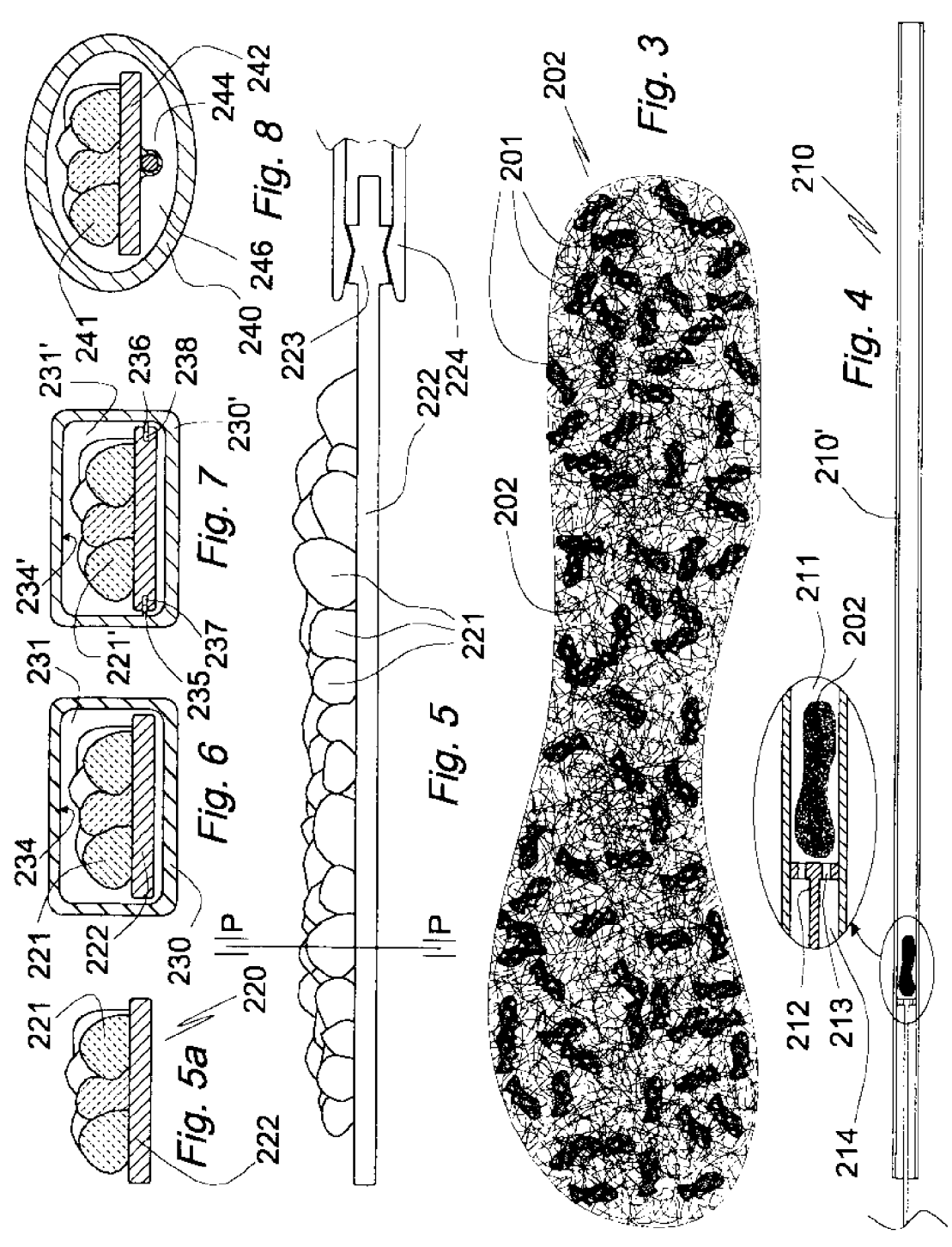

An exemplary fiber-supported cell aggregate 200 consisting of stem cells or embryological cells 201 in a non-woven web of polyglycolate fibers 202 is shown in FIG. 3. The aggregate 200 can be disposed in the lumen of a pipette or the distal compartment 211 of the lumen of a syringe 210 or a pipette provided with a piston 212 (FIG. 4). The piston comprises optionally perforations 213 extending in an axial direction to allow differences in liquid or gas pressure in the distal 211 and proximal 214 compartments of the syringe 210 to equalize, thereby preventing gas or fluid disposed in the distal compartment from erroneously being injected into the gel. Compartments 211, 214 may be filled with a gas, preferably air, optionally oxygen enriched air, or a suitable aqueous fluid such as an aqueous solution of gelatin or other biocompatible gel forming agent or artificial cerebrospinal fluid.

An exemplary layer of stem cells 221 adhering to and supported by a sheet 222 of cross-linked gelatin is shown in FIGS. 5 and 5a. At its rear end the sheet 222 is provided with a coupling profile 223 for releasable co-operation with an insertion instrument comprising pincers 224 at its distal end. The combination 220 of stem cells 221 and support 222 is disposed in the lumen 231 of a pipette 230 (FIG. 6). The pipette 230 and its lumen 231 are about rectangular in a radial section.

The modification of pipette 230 and the combination of 220 of stem cells 221 and support 222 of FIGS. 5, 5a shown in FIG. 7 comprises guide rails 235, 236 disposed on opposite inner faces of the pipette 230' wall co-operating with indentations 237, 238 in the lateral faces of the sheet 222. By this arrangement contact of the stem cell layer 221 with the inner wall of the pipette 230 and thus their possible damage is avoided.

The modification 240 of the pipette 230 of FIG. 6 shown in FIG. 8 is of ellipsoid form. The sheet 242 supporting a layer of stem cells 241 disposed in the pipette lumen 241 comprises an axially extending lead 244 attached to its face opposite to that to which layer of stem cells 241 is attached. The axially extending lead 244 can be one for light, such as a glass fiber, or an electrical conductor, such as for a microelectrode.

Example 7. Cell Aggregate and Tissue Fragment Implantation

Figures 2A, 2B:
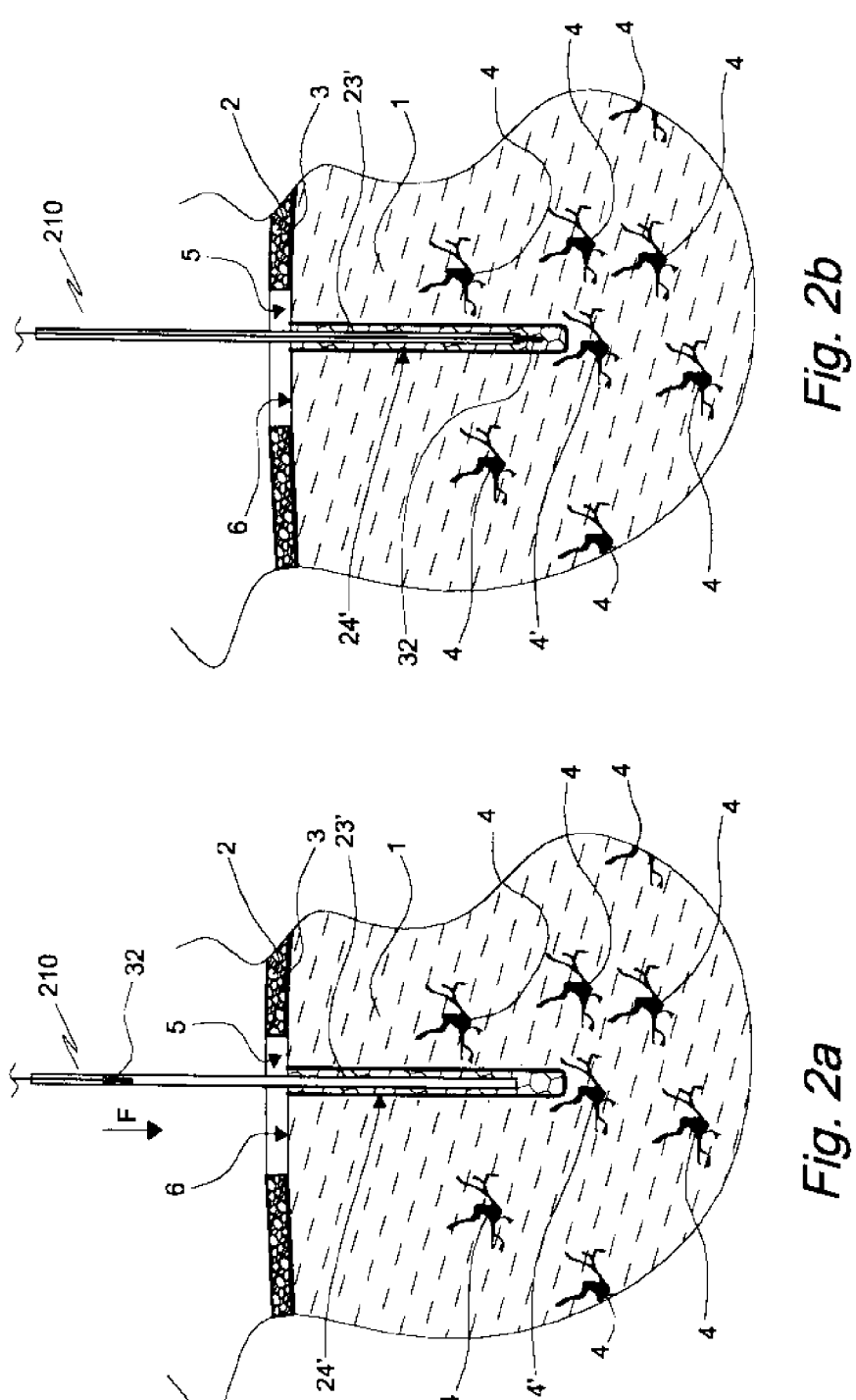

Implantation of a physically supported or stabilized cell aggregate 202 into brain tissue is shown in FIGS. 2a-2c. The cell aggregate 202 of FIG. 3 disposed in the lumen of a syringe in form of a tube 210 of constant diameter distally of a piston 212, which is displaceable within the tube (FIG. 4). The distal portion of the tube 210 is inserted into a channel 24' (FIG. 2a) filled with aqueous gel 23' to a desired depth. Then the cell aggregate 202 is displaced in a distal direction by further inserting the piston 212 into the tube 210 and finally expelled from the distal opening of the tube 201 into the gel 23'. The tube 210 can be filled with air, which escapes through perforations in the plunger 214, or with Ringer's solution or other infusion fluids. The tube 210 is then slowly withdrawn from the gel 23' leaving the cell aggregate 202 suspended in the viscous gel 23' (FIG. 2c). Alternatively the expulsion of cell aggregate 202 and withdrawal of the pipette or syringe tube or needle 210 proceeds simultaneously.

Access to the channel 24' from outside is then prevented by closing the opening in the tissue by a lid 32 of bone cement or rapid hardening tissue gel or other suitable material. Reference numbers in FIGS. 2a-2c not referred to in this section identify same elements as they do in FIGS. 1 through 1f.

In a preferred embodiment the tube 210 of the syringe or the tube of a pipette is positionally stabilized during implantation (FIG. 4a). The tube 210 is slidingly disposed in a tubiform guide element 219 of an insertion guide 215, the lumen of which is slightly wider than the tube 210 in an axial section. The tube 210 thus can be displaced axially but not radially in the tubiform guide element 219. At its distal (front) end the tubiform guide element 219 is provided with a firmly attached radially extending flange 217 in plane with the distal opening of the tube 210. The insertion guide 215 is mounted at a cylindrical channel 301 in soft tissue 300 filled with aqueous gel by disposing it in a manner so as to make its axis (not shown) about coincide with the axis (not shown) of the channel 301 and making its flange 217 abut the surface 216 of the tissue 300 surrounding the channel 301, then securing the insertion guide 215 positionally by means of firmly connecting it via a rigid holding element 218 attached to the tubiform guide element 219 with the person or animal or a support on which the person or animal is immobilized (not shown). Alternatively, the holding element 218 can be mounted at the proximally facing face of the flange 217 (not shown).

For disposition into a channel in soft tissue filled with aqueous gel an aggregate of stem or other cells 221 supported by and attached to a sheet 222 of a biocompatible material 222 such as native gelatin or cross-linked gelatin is disposed in the lumen 231 of a syringe or pipette 230 of constant inner diameter. The syringe or pipette 230 is of a radial section adapted to the form of the aggregate 221. The lumen thus is not preferably circular as with ordinary syringes or pipettes. In the embodiment of FIG. 6 the lumen 231 is about rectangular in cross section so as to be optimally adapted to the cross section of the combination of aggregate of cells 221 and support 222 shown in FIG. 5a.

The variety 230' of the syringe or pipette of constant diameter shown in FIG. 7 comprises means 235, 236, 237, 238 for protecting the cells 221' adhering to one face of a solid support 230' from contact with the portion of the syringe or pipette inner wall 234' facing the cells 221'. The means comprise rails 235, 236 extending in a longitudinal or axial direction protruding from opposite lateral inner walls of the syringe or pipette, the rails 235, 236 running in groves 237, 238, respectively in the lateral walls of the support sheet 230' extending in the same direction. In contrast, in the embodiment of FIG. 6 the cells 221 on the support 230 may touch the wall section 234 of the syringe or pipette 230 facing them, in particular when displacing the support 222 carrying the cells 221 during injection.

Figures 11, 11A:
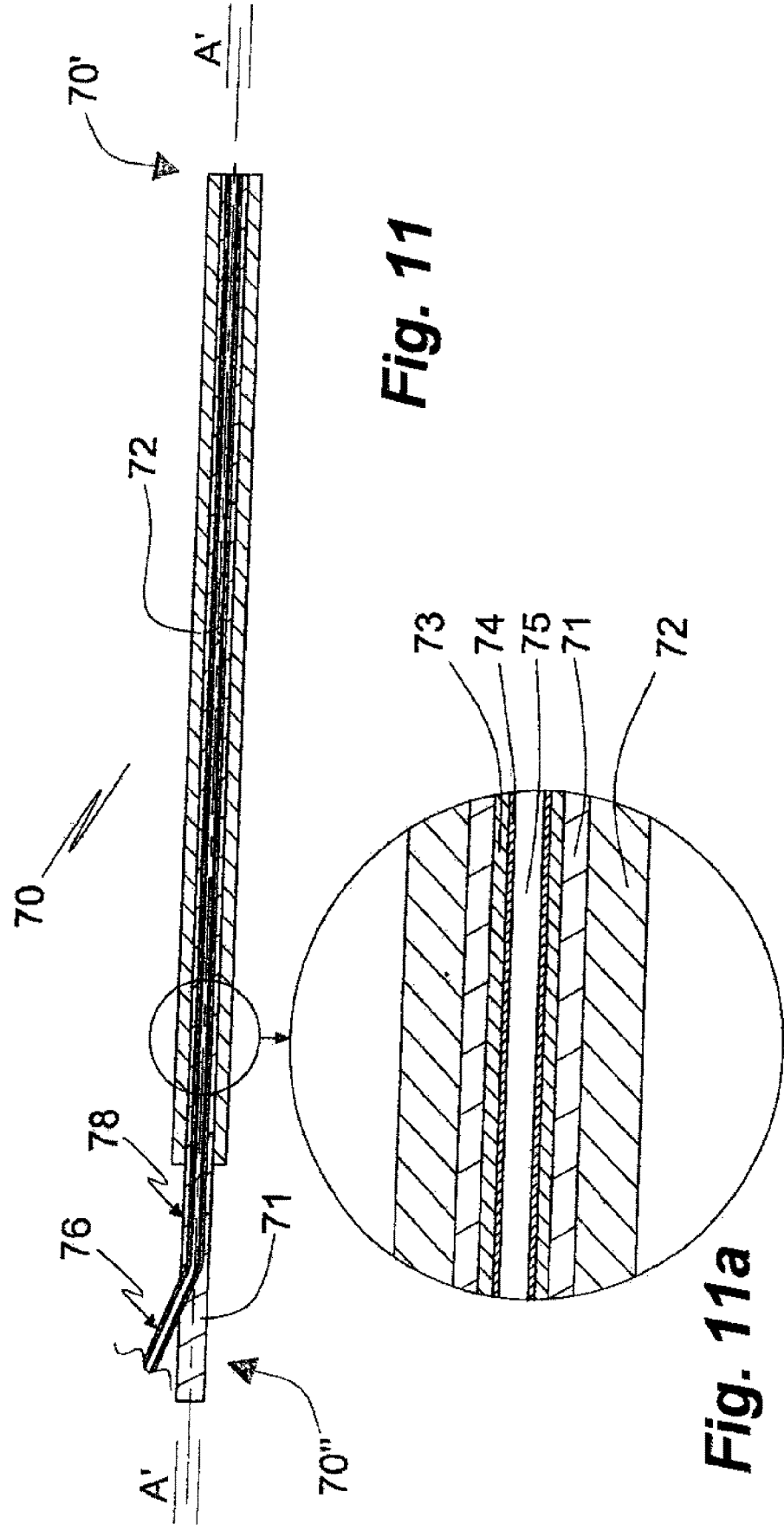
FIGS. 11-11a illustrate an apparatus according to the invention for forming a channel in nervous tissue filled with aqueous gel, in axial A*-A* (FIG. 7.

Example 8. Fourth Embodiment of the Apparatus According to the Invention, Comprising Fluid Passage Means for Distal Injection of Fluid A fourth embodiment 70 of the apparatus of the invention having a proximal end 70", a distal end 70' and a lateral cylindrical face 78 is shown in FIGS. 11 and 11a. It is a modification of the third embodiment of the apparatus of the invention in that it further comprises fluid passage means in form of a centered (axis A'-A') axially extending passage 75 in the pin 71. The substantially cylindrical passage 75 is formed by a flexible tube 73 disposed in an axial bore of the pin 71, the inner wall of the tube 73 being covered by a thin layer 74 of a metal of high conductivity, such as silver or gold. The layer 74 can serve as an electrode but can also be omitted. The flexible tube 73 is preferably of a transparent polymer material such as acrylate, and thus capable of conducting light and functioning as an optical fiber. At a short distance from the proximal end 70" of the apparatus 70 the flexible tube 73 is bent away from the central axis A'-A' so as to emerge from the lateral face 78 of the pin 71. A layer 72 of dry gelatin covers a portion of the lateral face 78 of the pin 71 extending from the frontal end 70' towards near the distal end 70" but does not cover the distal front face 77 of the pin 71 and thus not the distal opening of the passage 75.

The passage 75 can be used for injection of fluid material emerging at the distal end thereof. The fluid material can be, for instance, an aqueous solution of a pharmacologically active agent such as a neurotransmitter, for instance dopamine or acetylcholine or histamine. Alternatively or additionally, the passage 75 may be used for inserting a physically stabilized cell aggregate or tissue fragment of the invention into a channel in soft tissue filled with aqueous gel; in such case the cell aggregate or tissue fragment is disposed in the passage and displaced within the passage in a distal direction until it is expelled from the distal opening of the passage 75 into the aqueous gel. It is understood that the process of expelling the cell aggregate or tissue fragment from the pin into the aqueous gel has to wait at least until formation of the gel but it may be advantageous to wait for a longer time, such as for several hours or even days. It is within the ambit of the invention to similarly use the other embodiments of the apparatus according to the invention for injection of a physically stabilized aggregate of cells or soft tissue into the channel filled with aqueous gel.

Figures 12, 12A, 12B, 12C:
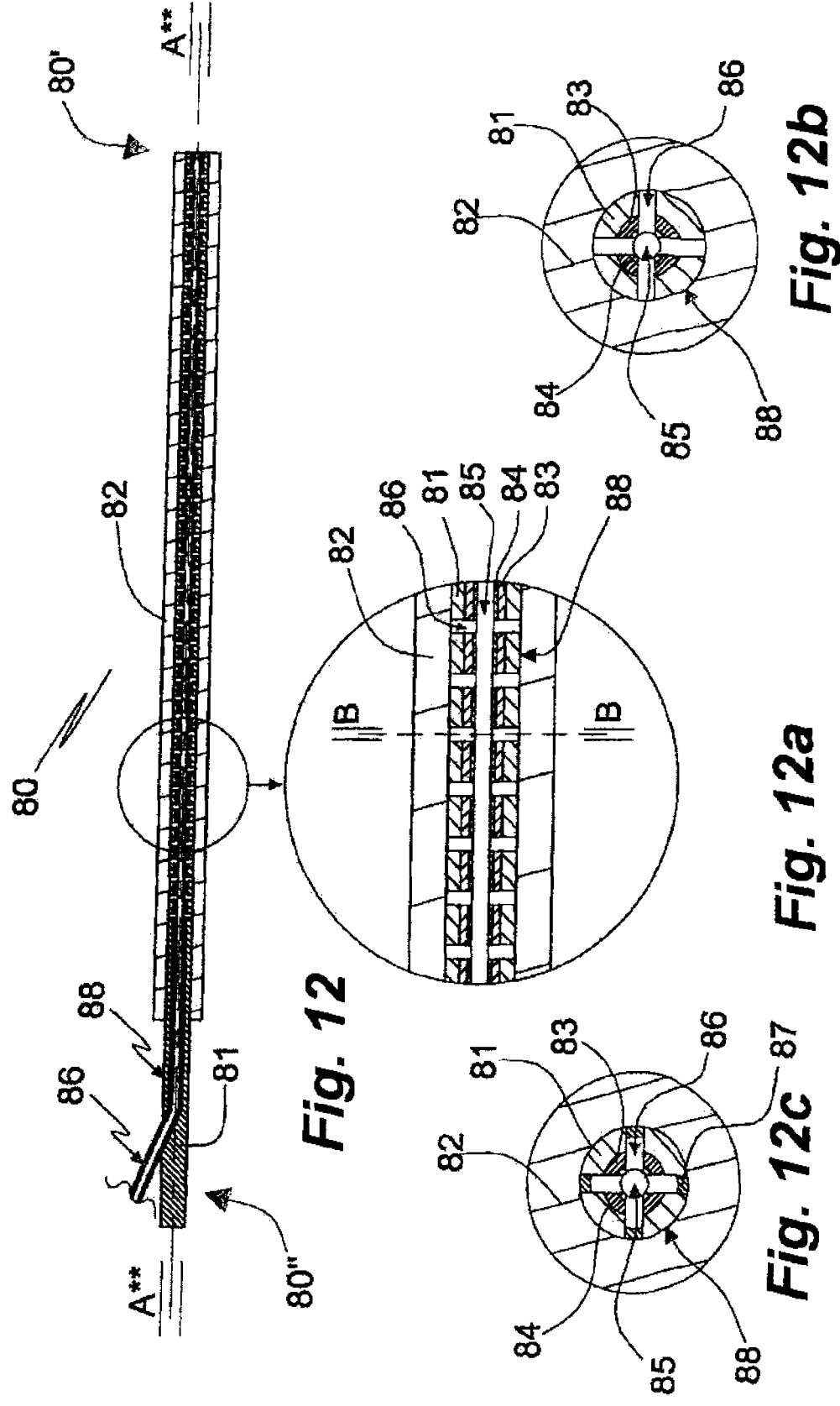
FIGS. 12-12c illustrate an apparatus according to the invention for forming a channel in nervous tissue filled with aqueous gel, in axial A-A (FIG. 8; 8a showing an enlarged portion thereof) and radial B-B (FIGS. 8b, 8c, further enlarged) section, the apparatus comprising, in addition to a cylindrical pin covered with dry gelatin and comprising optical fiber and electrode means, an axially extending passage in the pin for injection of fluid material into the channel from the opening of the passage at the distal face of the apparatus, and further comprising passages extending radially from the axially extending passage, the radially extending passages of a variety of the apparatus illustrated in dry FIG. 8c being plugged.

Example 9. Fifth Embodiment of the Apparatus According to the Invention Comprising Fluid Passage Means for Lateral Injection of Fluid A fifth embodiment 80 of the apparatus of the invention having a proximal end 80", a distal end 80' and a lateral cylindrical face 78 is shown in FIGS. 12, 12a, 12b. It is a modification of the fourth embodiment and comprises fluid passage means in form of a centrally disposed axially (axis A-A) extending channel 85 in the pin 81. The substantially cylindrical channel 85 is formed by a flexible tube 83 disposed in an axial bore of the pin 81, the inner wall of the tube 83 being covered by a thin layer 84 of a metal of high conductivity, such as silver or gold. The layer 84 can serve as an electrode but can also be omitted. The flexible tube 83 is preferably of a transparent polymer material such as acrylate, and thus capable of conducting light and functioning as an optical fiber. At a short distance from the proximal end 80" of the apparatus 80 the flexible tube 83 is bent away from the central axis A-A so as to emerge at the lateral face 88 of the pin 81. A layer 82 of dry gelatin of a water content of about 2% by weight covers the pin 81 extending from the proximal end 80' towards the distal end 80" but does not cover the distal front face 87 of the pin 81 comprising the distal opening of the flexible tube 83. Radially extending channels 86 are branching out from axial channel 85. They can be used for injection of fluid material emerging at the lateral face thereof upon transformation of the dry gelatin layer 82 to an aqueous gel. The fluid material can be, for instance, an aqueous solution of an agent accelerating the transformation of the dry gelatin layer 82 to an aqueous gel but may also or additionally comprise a pharmacologically active agent such as a neurotransmitter, for instance GABA, dopamine or acetylcholine or histamine. Cell aggregates or tissue fragments may be cooled during implantation to lower their metabolism, thereby improving cell survival.

The lateral channels 86 can also be used for sucking up fluid material, in particular during withdrawal of the pin 81 from tissue. The axially disposed channel 85 may be open or plugged at its distal end, the plug (not shown) consisting of a permanent material or one which is dissolved or degraded over time, such as cross-linked gelatin. Varieties of the fifth embodiment lacking the metal layer 84 are also comprised by the invention as are varieties lacking the flexible tube 83 or a portion thereof extending from the distal end 80' in a proximal direction; in such case the flexible tube 83 is substituted by a metal tube of high conductivity. The radially extending channels 86, such as four channels 86 disposed in a radial plane (FIG. 8b), extend from the axially disposed channel 85 through the flexible tube 83 and metal layer 84 walls but not through the dry gelatin layer 82. Peripheral terminal portions of the radially extending channels 86 may be plugged by plugs 87 (FIG. 12c) of a material dissolvable in an aqueous fluid; their provision facilitates covering the pin 81 with gelatin to form the dry gelatin layer 82 so as to avoid clogging the radially extending channels 86.

Example 10. First Modification of the Fifth Embodiment of the Apparatus According to the Invention Comprising a Friction Reducing Layer The embodiment 90 of the apparatus of the invention shown in FIGS. 13, 13*a*, 13*b*, 13*c* corresponds to the embodiment 80 of FIGS. 12, 12*a*, 12*b*, 12*c* except for that it comprises a friction reducing layer 89 on the dry gelatin layer 82' of same axial extension. Reference numbers 81' and 83' through 88' designate features of same kind as features 81 and 83 through 88 of the embodiment of FIGS. 12, 12*a*, 12*b*, 12*c*. Central axis A+-A+ corresponds to central axis A\*\*-A\*\* of FIG. 12. Reference numbers 90' and 90" designate the distal and proximal ends, respectively, of pin 81'. Section B+-B+ corresponds to section B-B of FIG. 12*a*.

Example 11. Second Modification of the Fifth Embodiment of the Apparatus According to the Invention Comprising a Friction Reducing Layer The embodiment 91 of the apparatus of the invention shown in FIG. 14 corresponds to the embodiment 80 of FIGS. 12, 12*a*, 12*b*, except for that it comprises two adjacent layers 92, 93 on the dry gelatin layer 82" of same axial extension as the total extension of layers 92, 93.

The proximally disposed layer 92 comprises a coagulant reducing bleeding from the channel formed by insertion of the apparatus 91 into nervous tissue, whereas the distally disposed layer 93 is a friction reducing layer, for instance one of glycoprotein based mucus, to minimize tissue damage during insertion of the pin 81". Reference numbers 82", 86" and 88" designate features of same kind as features 82, 86 and 88 of the embodiment of FIGS. 12, 12*a*, 12*b*. Central axis A++-A++ corresponds to central axis A\*\*-A\*\* of FIG. 12. Reference numbers 91' and 91" designate the distal and proximal ends, respectively, of pin 81".

Example 12. Embodiments of the Apparatus of the Invention of which the Pin is Covered with One or More Layers of Gel Forming Agent FIGS. 15, 15*a*, 15*b*, 15*c* illustrate, in a principal manner, an apparatus 100, 100*a*, 100*b*, 100*c* of the invention of which the cylindrical face of the pin 101, except for a portion extending for a short distance from the proximal end, is covered by of one or more layers of gel forming agent in varying disposition. In the embodiment 100 of FIG. 15 the pin 101 is covered by one layer 102 of gel forming agent. In the embodiment 100*a* of FIG. 15*a*, the pin 101 is covered by an inner layer 102 of gel forming agent covered by an outer layer 103 of gel forming agent. In the embodiment 100*b* of FIG. 15*b* the pin 101 is covered by a first layer 104 extending from the distal end thereof about halfway towards the proximal end, and by a second layer 102 abutting the proximal end of the first layer 104 and extending from there to near the proximal end of the pin 101. In the embodiment 100*c* of FIG. 15*c*, the pin 101 is covered by two inner layers 102, 104 disposed in the same manner as the layers of the embodiment of FIG. 11*b*, the inner layers 102, 104 being covered in turn by an outer layer 103.

Example 13. Embodiments of the Channel in Nervous Tissue of Invention Filled with One or More Layers of Aqueous Gel FIGS. 16, 16*a*, 16*b*, 16*c* illustrate, in a principal manner, a channel in nervous tissue 105 of the invention filled with one or more layers of aqueous gel 102\*, 103\*, 104\* formed from a corresponding layer of dry gel forming agent 102, 103, 104 on the pin 101 of the apparatus 100, 100*a*, 100*b*, 100*c* of the invention illustrated in FIGS. 16, 16*a*, 16*b*, 16*c*, respectively, by contact with aqueous body fluid exuded from nervous tissue 105. The channel of FIG. 16 is homogeneously filled with aqueous gel 102\*. The channel of FIG. 16*a* is filled with a central gel cylinder 102\* surrounded by a tubiform gel cylinder 103\* abutting the cylindrical tissue wall of the channel. A section extending from the bottom of the cylindrical channel of FIG. 16*b* to about half its height is filled with a first aqueous gel 104\*, the remaining upper portion of the channel being filled with a second aqueous gel 102\*. A central cylindrical portion of the channel of FIG. 16*c* is filled with first 104\* and second 102\* aqueous gel in the same disposition as in FIG. 16*b*, and is surrounded by a tubiform layer 103\* of aqueous gel extending over the combined height of layers 102\*, 104\*. By adapting the properties of a gel forming agent an aqueous gel of, for instance, desired viscosity or resistance to biological degradation, can be designed. It is also possible to incorporate non-gelling agents, such as pharmacologically active agent and nutrients in a dry gel forming layer to produce a corresponding aqueous gel comprising the non-gelling agent (s).

Example 14. Modification of the Method of the Invention

According to the invention it is feasible to use a pin of the apparatus of the invention comprising an axial passage, such as one disclosed in Examples 8 and 9, for injection of a physically stabilized aggregate of living cells or a soft tissue fragment into a channel in soft tissue filled with aqueous gel. The apparatus of Examples 8 and 9 can be combined with and inserted to a tubiform insertion guide having frontal and distal ends and comprising a means for immobilizing it in respect of the channel in soft tissue filled with aqueous gel into which the pin of the apparatus is inserted, such as the insertion guide disclosed in Example 2.

Example 15. Embryonic Tissue Culture

Tissue for implantation according to the invention can be either organ-like tissue cultured from stem cells or embryologic cells, or slices (fragments) of embryologic or juvenile brain or spinal tissue. Such tissue fragments or slices are cultured on extra-cellular material like cross-linked gelatin or Matrigel, a mixture of extracellular materials a large fraction of which is collagen. Use of the channel of the invention for such implantation creates a permissive environment for the implant in a host brain or spinal cord.

Tissue selected for implantation requires to be specifically prepared and free from pathogens for this purpose. One kind of preparation is culturing the tissue slice or fragment on a solid support suited for transfer from the culture medium to the gel in the channel. An attractive solution is to grow the implant on a support that can be directly transferred to the gel. The support functioning as a vehicle should advantageously be of a form so as to be disposable in the lumen of a cannula or pipette.

An attractive solution of the problem is to transfer the tissue onto a flat sheet of cross-linked gelatin and to cover it and at least the face of the sheet on which it has been disposed with a non-woven web of biocompatible fiber, the web being sufficiently loose to allow outgrowth of dendrites and axons. Particularly suitable fibrous materials other than cross-linked gelatin comprise silk and fibrin.

What is claimed is:

1. A system for performing a method for implantation of an implant selected from single living cells, aggregates of living cells, and tissue fragments, such as sheets of tissue with living cells into soft tissue, the system comprising:

an apparatus having an oblong rigid pin having a front end and a rear end and a layer comprising of dry gel forming agent disposed on a pin section extending from the front end in a distal direction and enclosing said section, wherein said layer or agent contains less than 20% by weight of water, wherein the pin is sufficiently rigid to allow the pin to be inserted into soft tissue in absence of the layer comprising of dry gel forming agent; and a syringe or pipette, wherein the method comprises, i) inserting the pin into soft tissue with the front end thereof foremost;

ii) allowing a channel filled with aqueous gel to be formed around the pin by contact of gel forming agent with aqueous body fluid;

iii) withdrawing the pin from the gel, iv) loading the implant in the syringe or the pipette;

v) inserting the syringe or the pipette into the gel;

vi) expelling the implant from the syringe of pipette into the gel; and vii) withdrawing the syringe or pipette from the gel, and wherein the implant comprises a support selected from any one of: sheet of biocompatible material, biocompatible fiber and combinations thereof, and a time difference between the provision of the channel and implantation is at least one minute.

2. The system of claim 1, wherein the soft tissue is neural tissue.

3. The system of claim 1, wherein the aqueous gel is selected from the group consisting of gel-forming protein, carbohydrate and glycoprotein.

4. The system of claim 1, wherein the aqueous gel is selected from the group consisting of gelatine, cross-linked gelatin, chemically modified gelatine, or recombinant gelatine.

5. The system of claim 1, wherein aqueous gel is selected from the group consisting of arabinogalactan, arabinoxylan, galactan galactomannan, lichenan, xylan, cellulose derivatives such as hydroxymethylpropyl cellulose, whey protein, soy protein, casein, hyaluronic acid, chitosan, gum Arabic, carboxyvinyl polymer, sodium polyacrylate, carboxymethyl cellulose, sodium carboxymethyl cellulose, pullulan, polyvinylpyrrolidone, karaya gum, pectin, xanthane gum, tragacanth, alginic acid, polyoxymethylene, polyimide, polyether, chitin, poly-glycolic acid, poly-lactic acid, copolymer of poly-glycolic and poly-lactic acid, co-polymer of poly-lactic acid and polyethylene oxide, polyamide, polyanhydride, polycaprolactone, maleic anhydride copolymer, poly-hydroxybutyrate co-polymer, poly(1,3-bis(p-carbophenoxy)propane anhydride), polymer formed by co-polymerization with sebacic acid or with poly-terephthalic acid, poly(glycolide-co-trimethylene carbonate), polyethylene glycol, polydioxanone, polypropylene fumarate, poly(ethyl glutamate-co-glutamic acid), poly(tert-butyloxy carbonylmethyl glutamate), poly-caprolactone, poly(caprolactone-co-butylacrylate), poly-hydroxybutyrate and copolymers thereof, poly(phosphazene); poly(D,L-lactide-co-caprolactone), poly(glycolide-co-caprolactone); poly(phosphate ester), poly(amino acid), poly(hydroxybutyrate), polydepsidpeptide, maleic anhydride copolymer, polyphosphazene, polyiminocarbonate, poly[(7.5% dimethyl-trimethylene carbonate)-co-(2.5% trimethlyene carbonate)], polyethylene oxide, hydroxypropylmethylcellulose, poly(ethylene-co-vinyl acetate); isobutylene-based copolymer of isobutylene and at least one other repeating unit such as butyl acrylate, butyl methacrylate, substituted styrene such as amino styrene, hydroxy styrene, carboxy styrene, sulfonated styrene, homopolymer of polyvinyl alcohol, co-polymer of polyvinyl alcohol and at least one other repeating unit such as a vinyl cyclohexyl ether, hydroxymethyl methacrylate, hydroxyl-or amino-terminated polyethylene glycol; acrylate-based copolymer such as methacrylic acid, methacrylamide, hydroxymethyl methacrylate, ethylene vinyl alcohol copolymer, silicone, based copolymer of aryl oralkyl siloxane and at least one repeating unit, polyurethane, heparan sulfate, RGD peptide, polyethylene oxide, chrondroitin sulfate, YIGSR peptides, keratan sulfate, VEGF biomimetic peptide, perlecan (heparan sulfate proteoglycan 2), lle-Lys-Val-Ala-Val (IKVAV) containing laminin alpha-1 chain peptide; modified heparin, fibrin fragments, hyaluronic acid, chemically modified hyaluronic acid, recombinant hyaluronic acid, and salts thereof.

6. The system of claim 1, wherein the aqueous gel comprises a pharmacologically active agent.

7. The system of claim 6, wherein the pharmacologically active agent is selected from the group consisting of neurotransmitter, such as GABA, dopamine, acetylcholine, histamine, coagulant, anticoagulant, antibiotic, osmotic pressure adjusting agent, anti-inflammatory agent, nutrient, factor stimulating growth, factor stimulating cell differentiation, hormone, immunosuppressive agent.

8. The system of claim 1, wherein the implant comprises any one of single living neural cells, aggregates of living neural cells or neural tissue fragments.

9. The system of claim 1, wherein the support is selected from one or more components selected from the group consisting of gelatine, arabinogalactan gel, arabinoxylan gel, galactan gel, galactomannan gel, lichenan gel, xylan gel cellulose derivatives such as hydroxymethylpropyl cellulose; gel forming protein such as whey protein, soy protein, casein; hyaluronic acid.

10. The system of claim 1, wherein the support are matrices selected from matrices comprising fibrous material and sheet of solid material, the matrices preferably being dissolvable or biodegradable, the fibrous material and sheet of solid material preferably selected from arabinogalactan gel, arabinoxylan gel, galactan gel, galactomannan gel, lichenan gel, xylan gel cellulose derivatives such as hydroxymethylpropyl cellulose; gel forming protein such as whey protein, soy protein, casein; hyaluronic acid, gelatine such as native and/or recombinant and/or cross-linked gelatine.

11. A method for implantation of an implant selected from single living cells, aggregates of living cells and tissue fragments into soft tissue comprising the application of a system, the system comprising: an apparatus having an oblong rigid pin having a front end and a rear end and a layer comprising of dry gel forming agent disposed on a pin section extending from the front end in a distal direction and enclosing said section, wherein said layer or agent contains less than 20% by weight of water, wherein the pin is sufficiently rigid to allow the pin to be inserted into nervous tissue in absence of its layer comprising of dry gel forming agent; and a syringe or pipette, wherein the method comprises, i) inserting the pin into soft tissue with its front end foremost;

ii) allowing a channel filled with aqueous gel to be formed around the pin by contact of gel forming agent with aqueous body fluid;

iii) withdrawing the pin from the gel, iv) loading the implant in the syringe or the pipette;

v) inserting the syringe or the pipette into the gel;

vi) expelling the implant from the syringe of pipette into the gel; and vii) withdrawing the syringe or pipette from the gel.

12. The method of claim 11, wherein a time difference between the provision of the channel and implantation is at least one minute.

* * * * *